(12) United States Patent
Ashby et al.

(10) Patent No.: US 7,645,212 B2
(45) Date of Patent: *Jan. 12, 2010

(54) SYSTEM AND METHOD FOR SELECTIVE ADJUSTMENT OF EXERCISE APPARATUS

(75) Inventors: Darren C. Ashby, Richmond, UT (US); Scott R. Watterson, Logan, UT (US); Kirk Lorrigan, Millville, UT (US); William T. Dalebout, Logan, UT (US)

(73) Assignee: Icon IP, Inc., Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/113,921

(22) Filed: Apr. 25, 2005

(65) Prior Publication Data

US 2005/0209052 A1 Sep. 22, 2005

Related U.S. Application Data

(63) Continuation of application No. 09/907,846, filed on Jul. 18, 2001, now abandoned, which is a continuation of application No. 09/496,560, filed on Feb. 2, 2000, now Pat. No. 6,447,424.

(51) Int. Cl.
*A63B 71/00* (2006.01)
(52) U.S. Cl. .................. 482/8; 482/1; 482/9; 482/54; 482/902
(58) Field of Classification Search ............... 482/1–9, 482/51, 54, 900–902; 434/247, 253; 601/23, 601/34; 463/3, 36, 43
See application file for complete search history.

(56) References Cited

U.S. PATENT DOCUMENTS

D211,801 S   7/1968   Quinton
3,518,985 A  7/1970   Quinton
3,592,466 A  7/1971   Parsons
3,602,502 A  8/1971   Hampl
3,659,845 A  5/1972   Quinton (Continued)

FOREIGN PATENT DOCUMENTS

EP          0199442      10/1986

(Continued)

OTHER PUBLICATIONS

American Express Workout Warehouse, Winter 1999, available on information and belief at least as early as Jan. 1999, 20 pages.

(Continued)

*Primary Examiner*—Glenn Richman
(74) *Attorney, Agent, or Firm*—Workman Nydegger

(57) ABSTRACT

An exercise system including a support base and an operable member movably coupled to the support base. Electrically coupled to the operable member is an interface console. The interface console includes a plurality of speed level keys and a plurality of grade level keys. The speed level keys enable a user to selected different pre-set speeds of the operable member, while the grade level keys enable a user to select different pre-set grades of the operable member. Associated with the speed level and grade level keys are incremental keys that enable a user to incrementally increase and/or decrease the speed, grade, or resistance of the exercise system.

43 Claims, 4 Drawing Sheets

U.S. PATENT DOCUMENTS

| | | | |
|---|---|---|---|
| 3,903,613 A | 9/1975 | Bisberg | |
| 4,082,267 A * | 4/1978 | Flavell | 482/6 |
| 4,120,294 A | 10/1978 | Wolfe | |
| 4,151,988 A | 5/1979 | Nabinger | |
| 4,278,095 A | 7/1981 | Lapeyre | |
| 4,358,105 A | 11/1982 | Sweeney, Jr. | |
| 4,408,613 A | 10/1983 | Relyea | |
| 4,504,055 A * | 3/1985 | Wells | 463/3 |
| 4,544,152 A | 10/1985 | Taitel | |
| 4,549,044 A | 10/1985 | Durham | |
| 4,571,682 A | 2/1986 | Silverman et al. | |
| 4,586,495 A | 5/1986 | Petrofsky | |
| 4,602,779 A * | 7/1986 | Ogden | 482/54 |
| 4,643,418 A | 2/1987 | Bart | |
| 4,659,074 A | 4/1987 | Taitel et al. | |
| 4,659,078 A | 4/1987 | Blome | |
| 4,671,257 A * | 6/1987 | Kaiser et al. | 601/34 |
| 4,687,195 A | 8/1987 | Potts | |
| 4,708,337 A | 11/1987 | Shyu | |
| 4,759,540 A | 7/1988 | Yu et al. | |
| 4,786,049 A | 11/1988 | Lautenschlager | |
| 4,790,528 A | 12/1988 | Nakao et al. | |
| 4,828,257 A | 5/1989 | Dyer et al. | |
| 4,842,266 A | 6/1989 | Sweeney, Sr. et al. | |
| 4,848,737 A | 7/1989 | Ehrenfield | |
| 4,860,763 A | 8/1989 | Schminke | |
| 4,869,497 A | 9/1989 | Stewart et al. | |
| 4,907,795 A | 3/1990 | Shaw et al. | |
| 4,919,418 A | 4/1990 | Miller | |
| 4,927,136 A | 5/1990 | Leask | |
| 4,938,474 A | 7/1990 | Sweeney et al. | |
| 4,949,993 A | 8/1990 | Stark et al. | |
| 4,959,713 A | 9/1990 | Morotomi et al. | |
| 4,976,435 A | 12/1990 | Shatford et al. | |
| 4,998,725 A | 3/1991 | Watterson et al. | |
| 5,020,795 A | 6/1991 | Airy et al. | |
| 5,037,089 A | 8/1991 | Spagnuolo et al. | |
| 5,054,774 A | 10/1991 | Belsito | |
| 5,062,632 A * | 11/1991 | Dalebout et al. | 482/7 |
| 5,067,710 A | 11/1991 | Watterson et al. | |
| 5,078,152 A | 1/1992 | Bond et al. | |
| 5,086,385 A | 2/1992 | Launey et al. | |
| 5,088,729 A | 2/1992 | Dalebout | |
| 5,089,960 A | 2/1992 | Sweeney, Jr. | |
| 5,104,120 A | 4/1992 | Watterson et al. | |
| 5,113,427 A | 5/1992 | Ryoichi et al. | |
| 5,142,358 A | 8/1992 | Jason | |
| 5,145,475 A | 9/1992 | Cares | |
| 5,149,084 A | 9/1992 | Dalebout et al. | |
| 5,195,935 A | 3/1993 | Fencel | |
| 5,213,555 A | 5/1993 | Hood et al. | |
| 5,290,205 A | 3/1994 | Densmore et al. | |
| 5,292,293 A * | 3/1994 | Schumacher | 482/4 |
| 5,299,810 A | 4/1994 | Pierce et al. | |
| 5,308,296 A | 5/1994 | Eckstein | |
| 5,313,942 A | 5/1994 | Platzker | |
| 5,314,391 A | 5/1994 | Potash et al. | |
| 5,323,784 A | 6/1994 | Shu | |
| D348,493 S | 7/1994 | Ashby | |
| 5,328,420 A | 7/1994 | Allen | |
| 5,328,422 A | 7/1994 | Nichols | |
| 5,352,166 A | 10/1994 | Chang | |
| 5,382,207 A | 1/1995 | Skowronski et al. | |
| 5,382,209 A | 1/1995 | Pasier et al. | |
| 5,403,252 A | 4/1995 | Leon et al. | 482/5 |
| 5,410,471 A | 4/1995 | Alyfuku et al. | |
| 5,410,472 A | 4/1995 | Anderson | |
| 5,431,612 A * | 7/1995 | Holden | 482/54 |
| 5,433,679 A | 7/1995 | Szymczak et al. | |
| 5,462,051 A | 10/1995 | Oka et al. | |
| 5,462,503 A | 10/1995 | Benjamin et al. | |
| 5,462,504 A | 10/1995 | Trulaske et al. | |
| 5,466,200 A | 11/1995 | Ulrich | |
| 5,474,090 A | 12/1995 | Begun et al. | |
| 5,476,430 A | 12/1995 | Lee et al. | |
| 5,489,249 A | 2/1996 | Brewer et al. | |
| 5,489,250 A | 2/1996 | Densmore et al. | |
| 5,512,025 A | 4/1996 | Dalebout et al. | |
| 5,518,471 A | 5/1996 | Hettinger et al. | |
| 5,527,239 A | 6/1996 | Abbondanza | |
| 5,527,245 A | 6/1996 | Dalebout et al. | |
| 5,535,664 A | 7/1996 | Rokowski | |
| 5,545,112 A | 8/1996 | Densmore et al. | |
| 5,547,439 A | 8/1996 | Rawls et al. | |
| 5,577,981 A | 11/1996 | Jarvik | |
| 5,591,104 A | 1/1997 | Andrus et al. | |
| 5,600,310 A | 2/1997 | Whipple, III et al. | |
| 5,619,412 A | 4/1997 | Hapka | |
| 5,619,991 A | 4/1997 | Sloane | |
| 5,626,539 A | 5/1997 | Piaget et al. | |
| 5,645,509 A | 7/1997 | Brewer et al. | |
| 5,645,513 A | 7/1997 | Haydocy et al. | |
| 5,674,453 A | 10/1997 | Watterson et al. | |
| 5,690,582 A | 11/1997 | Ulrich et al. | |
| 5,697,834 A | 12/1997 | Heumann et al. | |
| 5,702,323 A * | 12/1997 | Poulton | 482/8 |
| 5,713,794 A * | 2/1998 | Shimojima et al. | 463/36 |
| 5,720,771 A | 2/1998 | Snell | |
| 5,722,418 A | 3/1998 | Bro | |
| 5,733,228 A | 3/1998 | Stevens | |
| 5,738,612 A | 4/1998 | Tsuda | |
| 5,741,205 A | 4/1998 | Doll et al. | |
| 5,743,833 A | 4/1998 | Watterson et al. | |
| 5,749,372 A | 5/1998 | Allen et al. | |
| 5,752,883 A * | 5/1998 | Butcher et al. | 463/43 |
| 5,752,897 A | 5/1998 | Skowronski et al. | |
| 5,759,199 A | 6/1998 | Snell et al. | |
| 5,779,596 A | 7/1998 | Weber | |
| 5,785,630 A | 7/1998 | Bobick et al. | |
| 5,810,696 A | 9/1998 | Webb | |
| 5,810,747 A | 9/1998 | Brudny et al. | |
| 5,813,864 A * | 9/1998 | Ikuta | 434/253 |
| 5,820,525 A * | 10/1998 | Riley | 482/54 |
| 5,827,155 A | 10/1998 | Jensen et al. | |
| 5,830,113 A | 11/1998 | Coody | |
| 5,833,577 A | 11/1998 | Hurt | |
| 5,836,770 A | 11/1998 | Powers | |
| 5,845,230 A | 12/1998 | Lamberson | |
| 5,855,537 A | 1/1999 | Coody | |
| 5,857,939 A | 1/1999 | Kaufman | |
| 5,860,893 A | 1/1999 | Watterson et al. | |
| 5,860,894 A | 1/1999 | Dalebout et al. | |
| 5,865,733 A | 2/1999 | Malinouskas et al. | |
| 5,868,648 A | 2/1999 | Coody | |
| 5,873,369 A | 2/1999 | Laniado et al. | |
| 5,879,270 A | 3/1999 | Huish | |
| 5,880,677 A | 3/1999 | Lestician | |
| 5,888,172 A | 3/1999 | Andrus et al. | |
| 5,890,995 A * | 4/1999 | Bobick et al. | 482/4 |
| 5,899,834 A | 5/1999 | Dalebout et al. | |
| 5,905,442 A | 5/1999 | Mosebrook et al. | |
| 5,910,070 A * | 6/1999 | Henry et al. | 482/4 |
| 5,911,132 A | 6/1999 | Sloane | |
| 5,911,687 A | 6/1999 | Sato et al. | |
| 5,917,405 A | 6/1999 | Joao | |
| 5,929,748 A | 7/1999 | Odinak | |
| 5,931,763 A | 8/1999 | Alesandri | |
| 5,947,872 A | 9/1999 | Ryan et al. | |
| 5,961,561 A | 10/1999 | Wakefield, II | |
| 5,964,701 A | 10/1999 | Asada et al. | |
| 5,967,975 A | 10/1999 | Ridgeway | |
| 5,995,868 A | 11/1999 | Dorfmeister et al. | |
| 5,997,476 A | 12/1999 | Brown | |
| 6,004,243 A | 12/1999 | Ewert | |

| | | | |
|---|---|---|---|
| 6,010,451 A | | 1/2000 | Clawson |
| 6,013,007 A | * | 1/2000 | Root et al. ..................... 482/8 |
| 6,013,011 A | | 1/2000 | Moore et al. |
| 6,014,432 A | | 1/2000 | Modney |
| 6,022,272 A | * | 2/2000 | Sano ........................... 463/36 |
| 6,027,429 A | | 2/2000 | Daniels |
| 6,033,344 A | | 3/2000 | Trulaske et al. |
| 6,033,347 A | | 3/2000 | Dalebout et al. |
| 6,045,490 A | | 4/2000 | Shafer et al. |
| 6,050,822 A | | 4/2000 | Faughn |
| 6,050,921 A | | 4/2000 | Wang |
| 6,050,923 A | | 4/2000 | Yu |
| 6,050,924 A | | 4/2000 | Shea |
| 6,053,737 A | | 4/2000 | Babbit et al. |
| 6,053,844 A | | 4/2000 | Clem |
| 6,059,692 A | | 5/2000 | Hickman |
| 6,068,578 A | | 5/2000 | Wang |
| 6,103,203 A | | 8/2000 | Fisher |
| 6,106,297 A | | 8/2000 | Pollak et al. |
| 6,110,076 A | | 8/2000 | Hurt |
| 6,132,337 A | | 10/2000 | Krupka et al. |
| 6,132,340 A | | 10/2000 | Wang et al. |
| 6,152,856 A | * | 11/2000 | Studor et al. .................. 482/8 |
| 6,171,218 B1 | | 1/2001 | Shea |
| 6,174,268 B1 | | 1/2001 | Novak |
| 6,179,753 B1 | | 1/2001 | Barker et al. |
| 6,211,451 B1 | | 4/2001 | Tohgi et al. |
| 6,231,481 B1 | | 5/2001 | Brock |
| 6,231,482 B1 | | 5/2001 | Thompson |
| 6,234,936 B1 | | 5/2001 | Wang |
| 6,241,524 B1 | * | 6/2001 | Aoshima et al. ............ 434/118 |
| 6,244,988 B1 | | 6/2001 | Delman |
| 6,251,048 B1 | | 6/2001 | Kaufman |
| 6,280,362 B1 | | 8/2001 | Dalebout et al. |
| 6,283,896 B1 | | 9/2001 | Grunfeld et al. |
| 6,312,363 B1 | | 11/2001 | Watterson et al. |
| 6,322,451 B1 | | 11/2001 | Miura |
| 6,358,187 B1 | | 3/2002 | Smith |
| 6,447,424 B1 | | 9/2002 | Ashby et al. |
| 6,450,922 B1 | | 9/2002 | Henderson et al. ............. 482/8 |
| 6,572,512 B2 | | 6/2003 | Anderson et al. |
| 6,582,342 B2 | | 6/2003 | Kaufman |
| 6,626,803 B1 | | 9/2003 | Oglesby et al. |
| 6,712,737 B1 | | 3/2004 | Nusbaum |
| 6,761,667 B1 | | 7/2004 | Cutler et al. |
| 6,776,740 B1 | | 8/2004 | Anderson et al. |
| 6,783,482 B2 | | 8/2004 | Oglesby |
| 2002/0055422 A1 | | 5/2002 | Airmet et al. |
| 2005/0026750 A1 | | 2/2005 | Oglesby et al. |

FOREIGN PATENT DOCUMENTS

| | | |
|---|---|---|
| WO | 94/17860 | 8/1994 |
| WO | WO 98/00204 | 1/1998 |
| WO | WO 98/32496 | 7/1998 |

OTHER PUBLICATIONS

Reebok ACD4 User's Manual, copyright 1998, 34 pages.
"Best Values in Treadmills." Consumer Reports, Jun. 2003, 4 pages.
"Netpulse Brings Free Internet Access to Fitness Centers." Newsbytes.com, http://www.newsbytes.com, Jan. 17, 2000 (1 page).
"Precor and Netpulse Partner to Create the World's First Internet Powered Elliptical." Netpulse press release, Oct. 1, 1999 (2 pages).
"Stay Fit," Consumer Reports, available on information and belief at least as early as Feb. 2002, 8 pages.
"Surf While you Sweat." ABCNEWS.com, Oct. 27, 1998 (3 pages).
"The Best Products of 1999—Business Week's Top Picks of the Most Innovative Products on the Market." Business Week, Dec. 6, 1999 (2 pages).
"Treadmills & Ellipticals: Indoor exercise." Consumer Reports, Jan. 2005, 6 pages.
"Treadmills for Jogs and 'Walkouts.'" Consumer Reports, Jan. 1996, 5 pages.
"Workouts that Work," Consumer Reports, pp. 31-39, available on information and belief at least as early as Jan. 1999, 9 pages.
"Treadmills." Consumer Reports, available on information and belief at least as early as Oct. 1990, 8 pages.
"Treadmills." Consumer Reports, available on information and belief at least as early as Dec. 1997, 5 pages.
"Treadmills: More for the Money." Consumer Reports, Feb. 2004, 4 pages.
Consumer Reports.org—Treadmill ratings, Feb. 2004, 3 pages.
Brochure for Quinton Instruments, 1974, 34 pages.
Brochure for Genesis 3000, Technology for Total Fitness entitled "The Dynamic Answer to Home Fitness and Health" (© Genesis, Inc., Sep. 1985, 1 page without page number).
Brochure for Genesis 4000, Technology for Total Fitness entitled "The Modern Approach to Home Fitness and Health" (© Genesis, Inc., Sep. 1985, 2 pages without page numbers.
Brochure entitled "Technology for Total Fitness Genesis 3000", (© 1985 Genesis, Inc.) 7 pages.
Brochure entitled "Technology for Total fitness Genesis 4000", (© 1985 Genesis, Inc.) 5 pages.
Damark International, Inc. Mail Order Catalog, dated Nov. 17, 1994, cover page and p. 6.
Diaz, Francisco Jose, et al. "Evolucion de las caracteristicas fisicas y funcionales en jugadores de futbol soccer," Rivista de Investigacion Clinica, vol. 55, No. 5, Sep.-Oct. 2003, 528-534.
Healthrider: Softstrider-A Series (A60) User's Manual, Copyright 1999 ICON Health & Fitness, Inc., 26 pages.
Healthrider: Softstrider-A Series (A90) User's Manual, Copyright 1999 ICON Health & Fitness, Inc., 26 pages.
Heil, Daniel P. "Scaling of Submaximal Oxygen Uptake with Body Mass and Combined Mass During Uphill Treadmill Bicycling." Journal of Applied Physiology (Oct. 1998): 1376-1383.
Horizon Fitness Advance Series Treadmill Owner's Guide, pp. 1-40, available on information and belief at least as early as 2003.
Horizon Fitness Alpine Owner's Guide, pp. 1-29, available on information and belief at least as early as Aug. 2001.
Horizon Fitness Elite 2.0T, Elite 3.0T, Elite 4.0T, Elite 5.0T Treadmill Owner's Guide, pp. 1-40, available on information and belief at lease as early as 2004.
Horizon Fitness Horizon T20, Horizon T30, Horizon T40 Treadmill Owner's Guide, pp. 1-40, available on information and belief at least as early as 2004.
Horizon Fitness Paragon II Owner's Guide, pp. 1-27, available on information and belief at least as early as Aug. 2001.
Images from DVD movie, Rocky IV, scene 25, (including views of treadmill with inclining treadbase), and credit p. (1), and copyright p. (1), copyright 1985, 17 total pages.
Jakicic, J.M., et al. "The Accuracy of the TriTrac-R3D Accelerometer to Estimate Energy Expenditure." Medicine & Science in Sports & Exercise (May 1999): 747-754.
LifeFitness Website pages, available on information and belief at least as early as Oct. 2000, 12 pages.
McMorris, Megan, "Gear—Running in Place", Runner's World, Feb. 2006, 4 pages.
MedGraphics Cardiorespiratory Diagnostic Products http://www.medgraphics.com/products_main.html, printed Sep. 9, 2004, 2 pages.
Netpulse brochure. "Catch the wwwave," available on information and belief at least as early as Feb. 10, 2000 (6 pages).
Netpulse Club Watch™, Internet Powered Service, brochure, Apr. 1999.
Netpulse, Exercise station connects to the Net, Now you can sweat to the Net., www.netpulse.com, Sep. 1998.
Netpulse, Hop In, Log On and Sweat, Netpulse exercise machines are the latest Web feat, www.netpulse.com, Feb. 1999.
Netpulse, Ultra-Wired—Infotech is supposed to make life easier-remember? Here's how to be sure it does., www.netpulse.com, Aug. 1998.
Netpulse, Networkingout—Coming Distractions: Netpulse Helps Exercisers Surf the Net at the Gym Accomplish Several Goals at Once, www.netpulse.com, Apr. 1998.
Netpulse, New Fitness Equipment Combines Internet, Sweat, Now you can surf and sweat, www.netpulse.com, Jan. 1999.

Netpulse, Instead of having an equipment repair technician traveling over hill and dale, you may soon have equipment repaired via the internet, www.netpulse.com, Jul. 1998.
New Balance Fitness Equipment advertisement, *Runner's World*, Feb. 2006 1 page.
New Balance Fitness Equipment advertisement (with sport block dumbbell advertisement), *Runner's World*, Mar. 2006 1 page.
Proform Trail Runner Advertisement, copyright 2001, 1 page.
Robertson, Robert J., et al. "Gender Comparison of RPE at Absolute and Relative Physiological Criteria." Medicine and Science in Sports & Exercise, Dec. 2000, pp. 2120-2129.
Sears, Roebuck and Co., *Pro-Form 585TL Low Profile Treadmill, User's Manual*, Copyright 1996 (20 pages).
Shu-Lin Li. "The Effects of Beverage Containing Antioxidants and Carbohydrate Supplementation on Physiology and Blood Biochemisty in Endurance Exercise and Recovery Period." National College of Physical Education and Sports Taiwan Republic of China, 85 pages, 2001, (includes title page and English Abstract), and 3 pages of English translation.
Su-Jen Wang. "The Gait Analysis of Females with Flat foot and Normal foot in Walking and Running." National College of Physical Education and Sports Taiwan Republic of China, 134 pages, 2004 (includes title page and English Abstract).
Sweat.equity, Forbes.com, www.forbes.com, Feb. 1998.
T Series T3/T5 Treadmill Operation Manual, copyright 2001 LIfe Fitness (30 pages).
The Difference Between Surviving and Thriving May be as Simple as FitLinxx™, Fitlinxx Interactive Fitness Corp., brochure, 1998, 1 page.
The FitLinxx Interactive Fitness Network™, Fitlinxx Interactive Fitness Corp., brochure, 1998, 4 pages.
Advertisement, "We Just Made Buying a Trackmaster 100% Easier," *Athletic Business*, Oct. 1991, 2 pages.
Advertisement, "Trackmaster TM500E Treadmill Features Interactive Controller," *Athletic Business*, Oct. 1991, 1 page.
Advertisement, "Survival Equipment for the New Age," *Athletic Business*, Oct. 1991, p. 60.
Advertisement, "Introducing the LifeStep Model 9500—We've Made the Best Even Better," *Athletic Business*, Sep. 1991, 1 page.
Advertisement, "We Just Made Buying a Trackmaster 100% easier," *Athletic Business*, Sep. 1991, 2 pages.
Trackmaster Online http://web.archive.org/web/19991012091810/http://www.trackmastertreadmills.com, available on information and belief at least as early as Oct. 1999, 2 pages.
Trackmaster Online: History http://web/archive.org/web/19991012112927/www.trackmastertreadmills.com/history.html, available on information and belief at least as early as Oct. 1999, 1 page.
Trackmaster Online: Treadmill Controllers: http://web.archive.org/web/20010124093300/www.trackmastertreadmills.com/contrlr.html, available on information and belief at least as early as Jan. 2001.
Trackmaster Online: Treadmills http://web.archive.org/web/19991012162015/ www.trackmastertreadmills.com/treadmills.html, available on information and belief at least as early as Oct. 1999, 2 pages.
Trackmaster Online: Treadmills http://web.archive.org/web/20010819045524/www.trackmastertreadmills.com/500.htm, available on information and belief at least as early as Aug. 2001, 2 pages.
Trackmaster Online: Treadmills http://web.archive.org/web/20010819045539/www.trackmastertreadmills.com/500controla.htm, available on information and belief at least as early as Aug. 2001,2 pages.
Trackmaster Online: Treadmills http://web.archive.org/web/20010815085501/www.trackmastertreadmills.com/treadmills.html, available on information and belief at least as early as Aug. 2001, 2 pages.
Trackmaster TM500-E AC Owner's Manual Operation & Maintenance guide, pp. 1-52, available on information and belief at least as early as Jan. 2001.
Trackmaster Treadmill Manual, p. 8, "Control Box and Functions."
Treadmill Owner's Manual by Formula 22100 Manual Treadmill, upon information and belief, available at least as early as 1998, 20 pages.
Treadmills Rating @ Treadmill Warehouse.net, http://www.treadmillwarehouse.net/affordable-treadmills-running-walking-fitness-equipment-exercisers-rating.htm, printed Feb. 24, 2006, 2 pages.
Treadmills' Ratings, http://web.archive.org/web/20010505011643/www.treadmillwarehouse.net/rating.htm, available on information and belief at least as early as May 2001, 3 pages.
Trotter Advertisement: "Introducing the 575 Club Trainer: One Piece of Equipment for Walking, Jogging, Running, and Climbing," available on information and belief at least as early as 1992, 2 pages.
U.S. Appl. No. 60/152,657, filed Sep. 7, 1999 to James B. Fox, et al, entitled Exercise Treadmill (73 pages).
U.S. Appl. No. 60/159,268, filed Oct. 13, 1999 to Thomas F. Smith, Jr., et al., entitled Exercise Treadmill (6 pages).
Wen-Chi Chen. "The Biomechanical Study of Normal Foot and Flat Foot in Walking and Running.", 113 pages, 2002, (includes title page and English Abstract).
Weslo Cadence 1020 User's Manual, copyright 1998 ICON Health & Fitness, Inc., 18 pages).
"Trackmaster Introduces the All-New TMX Series Treadmills; Longer, Wider, Quieter, and Packed with User Preferred Features," National Fitness Trade Journal, Fall 2001, 4 pages.
"Absolutely Motivating. Exceptional Performance. Trademark Feel." ExerTools. *Training & Conditioning*, Nov. 1999, vol. IX, No. 8, 1 page.
"HR Clubtrack," Quinton Fitness Equipment. *Training & Conditioning*, Feb. 1998, vol. VIII, No. 1, 1 page.
Photographs of Trackmaster Treadmill TM500, SER. 12165 AC, which was available on information and belief, at least as early as 1995 (11 photographs).
DVD containing video images of Trackmaster Treadmill TM500, SER. 12165 AC, which was available, on information and belief, at least as early as 1995 (approximately eleven minutes).
Photographs of Trackmaster Treadmill TM500/S, SER. 9756, which was available, on information and belief, at least as early as 1994 (9 photographs).
Amendment "C" dated Jan. 24, 2007, Examiner Interview, p. 17 (1 page).
Office Action dated Jun. 25, 2004 from U.S. Appl. No. 09/907,846 (7 pages).
Notice of Allowance dated Feb. 4, 2005 from U.S. Appl. No. 09/907,846 (4 pages).
Issue Notification from U.S. Appl. No. 09/907,846 (1 page).
Petition Granted Notification from U.S. Appl. No. 09/907,846 (2 pages).
Notice of Allowance dated Jan. 26, 2006 in U.S. Appl. No. 09/907,846 (5 pages).
Notice of Abandonment dated May 31, 2006 in U.S. Appl. No. 09/907,846 (2 pages).
Office Action dated Feb. 22, 2001 in U.S. Appl. No. 09/496,560 (5 pages).
Notice of Allowance dated Apr. 8, 2002 in U.S. Appl. No. 09/496,560 (3 pages).
Issue Notification dated Aug. 22, 2002 in U.S. Appl. No. 09/946,560 (1 page).
Notice of Allowance dated Oct. 22, 2001 in U.S. Appl. No. 09/496,560 (2 pages).
Trackmaster Online: Treadmills http://web.archive.org/web/1999101262015/ www.trackmastertreadmills.com/treadmills.html, available on information and belief at least as earl as Oct. 1999, 2 pages.
Trackmaster Online: Treadmills http://web.archive.org/web/20010819045524/www.trackmastertreadmills.com/500.htm, available on information and belief at least as early as Aug. 2001, 2 pages.
Trackmaster Online: Treadmills http://web.archive.org/web/20010819045539/www.trackmastertreadmills.com/500controla.htm, available on information and belief at least as early as Aug. 2001,2 pages.
Trackmaster Online: Treadmills http://web.archive.org/web/20010815085501/www.trackmastertreadmills.com/treadmills.html, available on information and belief at least as early as Aug. 2001,2 pages.

Trackmaster TM500-E AC Owner's Manual Operation & Maintenance guide, pp. 1-52, available on information and belief at least as early as Jan. 2001.

Treadmill Owner's Manual by Formula 22100 Manual Treadmill, upon information and belief, available at least as early as 1998, 20 pages.

Treadmills Rating @ Treadmill Warehouse .net, http://www.treadmill warehouse.net/affordable-running-walking-fitness-equipment-exercsers-rating.htm, printed Feb. 24, 2006, 2 pages.

Treadmills' Ratings, http://web.archive.org/web/20010505011643/www.treadmillwarehouse.net/rating.htm, available on information and belief at least as early as May 2001, 3 pages.

Transcript of Deposition of Michael Benjamin, taken Apr. 11, 2007, from *Cybergym Reaserch, LLC* v. *Icon Health & Fitness*, et al., in the Eastern District f Texas, Marshal Dividion, Case No. 2:05-cv-527 DF, 33 pages.

Michael Benjamin Computation Book, dated Nov. 2, 1991, 14 pages.

Tectrix Fitness Equipment, VR Bike Owners Manual, Jan. 1995, 19 pages.

Tectrix Fitness Equipment, VR Bike Maintenance and Repair manual, Mar. 1997, 55 pages.

Tectrix Fitness Equipment, Photographs of VR Bike, available on information and belief at least as early as 1994, 13 pages.

Tectrix, *Tectrix Fitness Equipment History*, Jim Sweeney, Jun. 20, 1996, 4 pages.

Tectrix Fitness Equipment, *Are We Having Fun Yet?* brochure, 1995, 4 pages.

First for Women, No More Bicycle Boredom, Oct. 3, 1994, 2 pages.

Sports Illustrated, Software for Hardbodies, Sep. 19, 1994, 2 pages.

Cybergear, Inc., *CyberGear 1000* brochure, which was available, on information and belief, as least as early as 1994, 2 pages.

National Fitness Trade Journal cover, Fall 1995, 1 page.

Tectrix Fitness Equipment, *The Body the Brain the Passion the Will* product brochure, circa 1998, 24 pages.

Leisure Management, Going Downhill, Virtually, vol. 14, No. 8, Aug. 1994, 2 pages.

Tectrix Fitness Equipment, *Sweeney Town from CyberGear for the Tectrix VRBike* brochure, which was available, on information and belief, at least as early as 1994, 2 pages.

Trackmaster Treadmill Manual, p. 8, "Control Box and Functions," available, on information and belief, at least as early as 2004, 1 page.

DVD labeled "Tectrix VR Bike videos, including: 1)Media Coverage News Clips of Tectrix VR Bike, dated Jun. 15, 1994, 11 minutes, 19 seconds; 2) Video demonstrating use of CyberGEAR exercise bike, which was available, on information and belief, at least as early as 1994, 5 minutes, 39 seconds; and 3) Video demonstrating use of Tectrix VR Bike, which was available, on information and belief, at least as early as 1994, 4 minutes, 43 seconds.".

"Virtual Treadmill Takes Users Anywhere They Want to Go," http://www.ksl/com/?nid=148&sid=6920538, Jun. 24, 2009, 2 pages.

Athletic Business, Tectrix Fitness Equipment, Jul. 1997, 1 page.

"Defendant's Amended Invalidity Contentions," Case No. 2:05-cv-527, signed by Kirk Harris on Mar. 16, 2007.

"Icon Health & Fitness Inc.'s Supplemental Preliminary Invalidity Contentions," Case No. 2-05-cv-527, signed by Brent A. Hansen on Jun. 23, 2006.

"Icon Health & Fitness Inc.'s Preliminary Invalidity Contentions," Case No. 2-05-cv-527, signed by Brent A. Hansen on Jun. 26, 2006.

"Expert Report of Dr. Brent Nelson Pursuant to Federal Rule of Civil Procedure 26(a)(2)(B)," Mar. 13, 2007.

* cited by examiner

SYSTEM AND METHOD FOR SELECTIVE ADJUSTMENT OF EXERCISE APPARATUS

RELATED APPLICATIONS

This application is a continuation of U.S. patent application Ser. No. 09/907,846, Filed Jul. 18, 2001 now abandoned, entitled "System and Method for Selective Adjustment of Exercise Apparatus" to Ashby, et al, which is incorporated herein in its entirety by reference and which is a continuation of U.S. patent application Ser. No. 09/496,560, Filed Feb. 2, 2000, now U.S. Pat. No. 6,447,424 entitled "System and Method for Selective Adjustment of Exercise Apparatus" to Ashby, et al, which is incorporated herein in its entirety by reference.

BACKGROUND OF THE INVENTION

1. The Field of the Invention

The invention is in the field of electronic controllers for exercise equipment. More specifically, this invention relates to a method and system for selective adjustment of an exercise apparatus to simulate movement along a desired pathway.

2. The Relevant Technology

The desire to improve health and enhance cardiovascular efficiency has increased in recent years. This desire has been coupled with the desire to exercise in locations that are compatible with working out within a limited space such as within an individual's home or exercise gym. This trend has led to an increased desire for the production of exercise equipment. Furthermore, in modern urban society, it has become more and more difficult for the average individual to experience the exhilaration of exercising in nature. To compensate for this difficulty, athletic sports gyms and exercise facilities featuring treadmills, bicycles or exercise bicycles, weights, and stair stepper machines, have been developed in great abundance.

Climbing devices have also become very popular in recent years. Climbing requires a user to raise the user's knees in continual, strenuous strides. Climbing typically requires more exertion than mere walking on a flat surface. Consequently, the exercise of climbing can provide a more intense, challenging workout. Climbing exercise apparatuses typically feature an endless moving assembly, which is set on a significant angle and has a series of foot supports or steps. This configuration allows the exerciser to simulate the movements of climbing, walking, or running up a steep incline. Angled, moving staircase-type devices are typical examples of such climbing apparatuses.

Unfortunately, typical climbing devices within the art are tall and often require more ceiling height than is available in an exerciser's home. Thus, such climbing devices generally require a gym or warehouse, or at least a vaulted ceiling. Treadmill devices that fit into a user's home generally incline from a neutral position to an inclined position, then decline back to the neutral position. However, typical treadmill devices fail to adequately provide a user with the kind of terrain experience encountered when ambulating over rocky, rough, and natural terrain. For example, a hiker traversing a hiking trail typically exhibits greater lateral movement than most treadmill belts presently allow. Furthermore, beginning at around a 15% grade, a hiker exercising on a treadmill can start producing more energy than is necessary to drive the treadmill belt, such that a braking system is desirably employed. These structural, systematic requirements are presently not considered in the design of modern treadmills.

What is needed is a controller on an exercise apparatus that simulates the dynamics of natural terrain with its accompanying slopes and inclines and can fit into a user's home or another location with a limited ceiling height. Unfortunately, controllers presently associated with these exercise devices are only capable of creating an artificial time based environment. Generally, these exercise devices use an indicator to demonstrate the increase in workout difficulty as a treadmill increases its inclination or a stair stepper becomes more difficult to climb. These devices are exclusively time based, meaning that no matter how slowly an individual is walking, after a certain amount of time, an artificial hill displayed will pass. Unfortunately, time based regulation does not accurately simulate the environment that exists in a real hike or a real walk, depriving the individual of the substantial health benefits associated with a cardiovascular workout based substantially on a natural setting.

Exercise devices that utilize artificial mountain profiles typically create mountains of speed or of incline. Usually, these artificial profiles are time based workouts, where at a preprogrammed time in the workout, the exercise apparatus moves a little faster or increases the resistance, and then during the next workout segment the device alters its operating parameters again. Eventually, the device works its way up to a maximum speed, maximum incline, or maximum workout. Accordingly, the artificial profile adjusts the exercise apparatus so that the next segment becomes less difficult or more difficult by changing the resistance, inclination, or speed. As such, the typical exercise device goes through preset profiles. However, the artificial mountain or hill segments are simply time-based alterations of resistance, speed or inclination. Thus, typical workouts lack the natural diversity provided by a mountain trail.

The natural diversity provided by mountain trails yields additional incentives for a user to complete a workout. Representative exercise devices lack these incentives when their workouts are based purely on artificial workout profiles.

Finally, users of existing climbing exercise devices are increasingly faced with the difficulty of interpreting multiple monitoring panels with a single glance during the workout, resulting in sensory overload for the user. Most controllers contain separate indicators for distance traveled, vertical feet traversed, remaining workout length, and relative grade or incline adjustments to be made. It is difficult for a user to interpret and understand all of these gauges with one glance.

SUMMARY OF THE INVENTION

It is therefore an object of this invention to provide a method and system that electronically simulates a mountain hike.

It is another object of this invention to provide a method and system for converting a topographical map to an actual exercise workout for use with an exercise device that can vary between a variety of grades.

It is a further object of the invention to allow the user direct adjustment control of grade and speed, as well as tracking vertical feet hiked and the overall distance and speed.

It is a further object of the invention to provide exercise devices such as hiking apparatuses, climbers, treadmills, exercise bicycles, skiers, aerobic ellipticals, rowing devices, steppers and other devices that can simulate mountain trails, mountain streams, or rough terrain through an adjustment in resistance, incline, or speed.

It is another object of the invention to provide a controller which controls a workout that is both time and distance based, thereby allowing an individual to hike at their own pace and ensuring that they adequately follow a realistic mountain trail length.

It is another object of the invention to provide a single glance panel containing graphic representations because the user is only be minimally distracted from a workout.

It is another object of the invention to provide a carefully designed graphical representation panel allowing the user to obtain all of the important information with one glance.

These and other objects of the invention, as will be apparent herein, are accomplished by generating a mountain exercise profile having trail workout segments that are digitally coded to enable a selectively adjustable exercise device. A selectively adjustable exercise system comprises a virtual trail system for use on a selectively adjustable exercise apparatus.

Aside from being electrically coupled to the selectively adjustable exercise device and a display device, a controller of the virtual trail system operates according to software based workout profiles. The software interprets feedback from the exercise device and a user interface console to generate control signals for motors, electronic braking systems, and user monitors associated with the virtual trail system. The control signals for the exercise device components and display device panels are compiled into workout profiles for use by the controller. Other features of the exercise system include the incorporation of direct adjustment keypads on the user interface console for grade and speed settings. These keypads are primarily used when the system is not recalling a preprogrammed workout routine or hiking trail and is under manual control.

These and other objects and features of the present invention will be more fully apparent from the following description and appended claims, or may be learned by the practice of the invention as set forth herein.

BRIEF DESCRIPTION OF THE DRAWINGS

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The invention is described below by using diagrams to illustrate either the structure or processing of embodiments used to implement the systems and methods of the present invention. Using the diagrams in this manner to present the invention should not be construed as limiting of its scope. The present invention contemplates both methods and systems for selective adjustment of exercise equipment.

One embodiment of a virtual trail system of the present invention comprises: (i) an interface means for receiving workout related control inputs from the user of the exercise equipment; (ii) processor means for electronically computing operational information based at least on part on control inputs received from the interface means; (iii) feedback means for conveying information concerning the amount of exercise performed by the user to the processor means; (iv) indicator means for displaying workout information to the user adapted for indexing travel along the length of a workout trail from segment checkpoint to segment checkpoint until the end of the trail; and, preferably, (v) control means associated with the processor means for causing the indicator means in response to information from the feedback means to travel along the workout trail at a rate proportional to the rate of which exercise is performed by the user.

Figure 1:
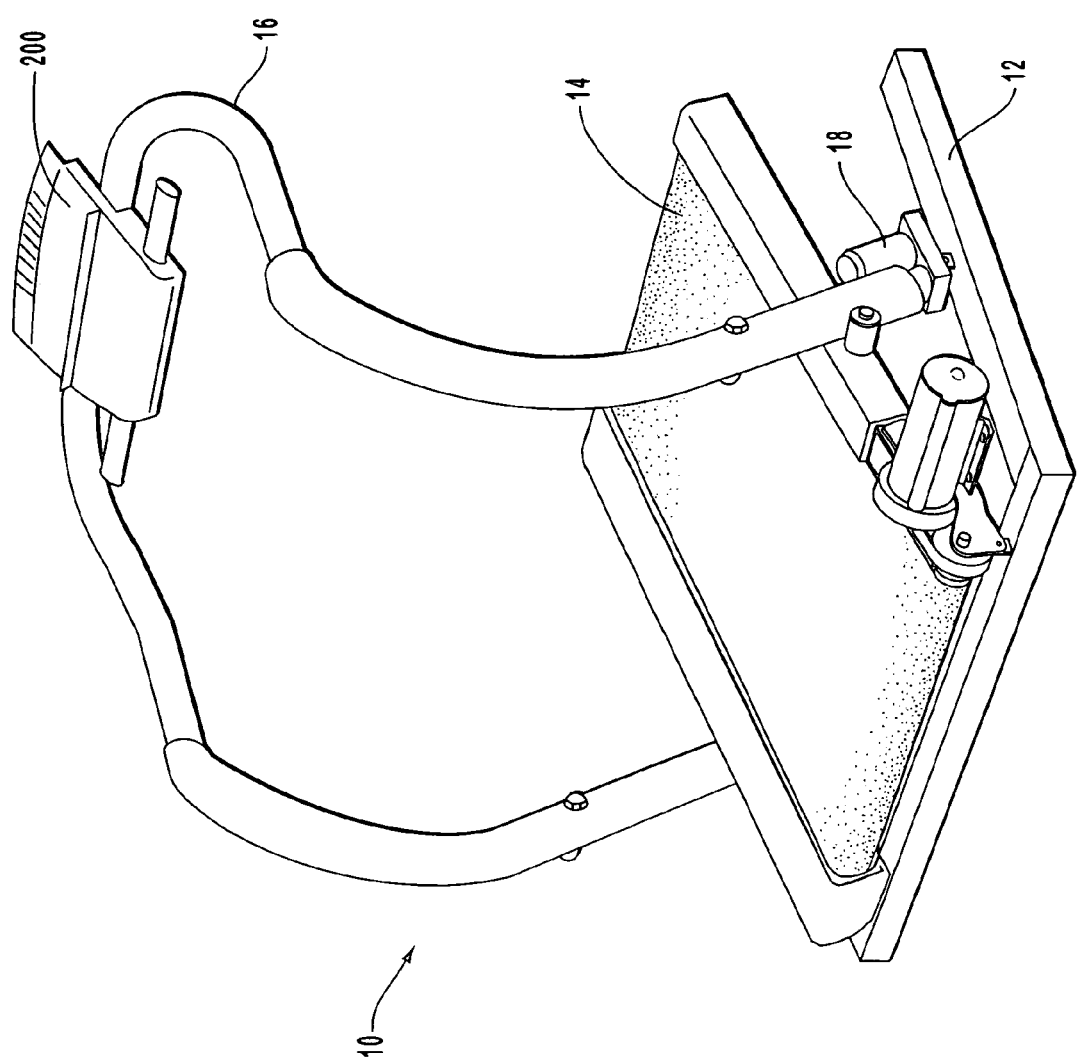
FIG. 1 illustrates a selectively inclining exercise system.

This virtual trail system may be used in a wide variety of selectively adjustable exercise equipment. For example, in one embodiment as depicted in FIG. 1, the virtual trail system is associated with a hiking exercise apparatus. The virtual trail system may also be employed on variety of other hiking exercise apparatuses, such as those identified in U.S. patent application to Cutler, et al entitled "Hiking Exercise Apparatus," filed on Feb. 2, 2000, which is incorporated herein in its entirety by reference.

In addition to treadmills, alternative embodiments include associating the virtual trail system with an exercise cycle, an elliptical aerobic apparatus, a stair stepper, a skiing device, rowing equipment, and other exercise devices, can also simulate mountain trails, mountain streams, or rough terrain. Each of these exercise equipment embodiments would require unique components as previously designated to provide the necessary adjustment in resistance, incline, or speed. However, many of the embodiments contain considerable crossover for their respective applications.

For example, an exercise cycle can very easily use a mountain biking trail to create a similar experience as a hiker might experience on a treadmill or stair stepper. One difference in the hiker and bicycle embodiments would be that the exercise cycle can either increase the resistance or physically move the exercise cycle in an up and down fashion.

An embodiment based on a skiing device can use mountain cross-country ski trails and either adjust actual grade or alter the resistance. A rowing device can simulate mountain streams or rivers by adjusting rowing resistance or restricting the rowing action.

The mountain exercise profile may use topical maps, GPS coordinates, or portable monitors to design the actual exercise program. A trail workout designer can plot a trail over a mountain area on a topographical map and a profile of the incline changes over the terrain will be created. Workout segments can be created which average the slope change for that distance, resulting in multiple grade changes according to the trail segment.

Figure 2:
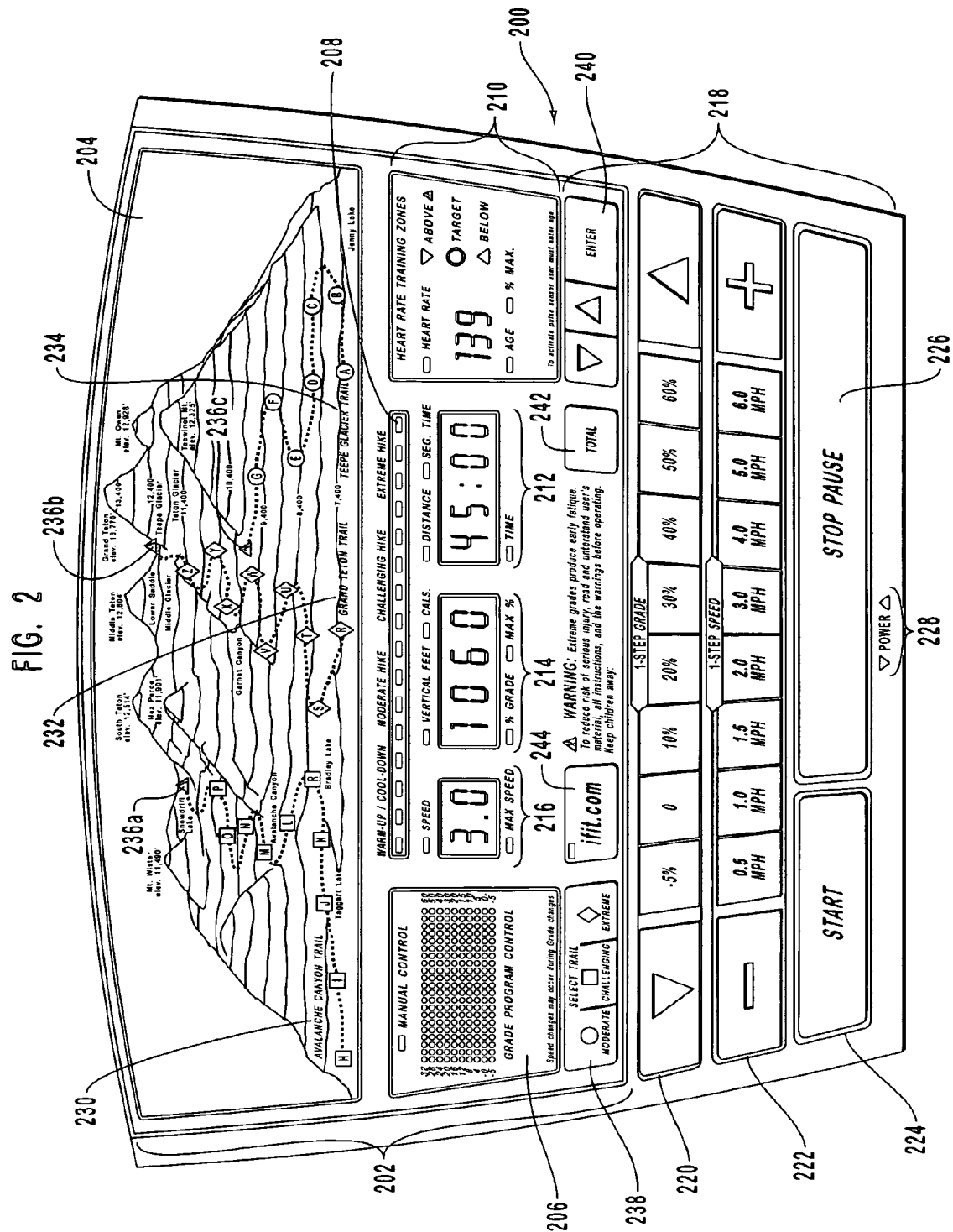
FIG. 2 is a motivational display device configured with three workout profiles created from actual trails in the Grand Teton mountain range and terrain.

In FIG. 2, examples of such workout segments are designated as the trail between the alphabetical markers on each trail. An alternative embodiment allows for workout segments to be subdivided for multiple grade adjustments. These workout segments are combined into a workout profile. Following a review of the workout profile by a trainer, the trail workout designer will be able to identify the density of the trails and alter the workout segment lengths in order to fit a similar trail workout on to the specified exercise device. Specifically, the trail workout designer creates variable segment lengths that best compare to the natural hike, including gradual incline segments, short steep segments, and short negative grade segments. A trail workout designer can also use GPS coordinates in conjunction with a master topographical map to create a successful workout trail. Midway or rest points may also be incorporated into a workout trail at the end of a workout segment.

Monitor devices enable a hiker to carry the monitor on an actual hike and record the distance and inclination walked by the user, and then apply that particular hike to the exercise machine software. This allows the user to exercise on weather prohibitive days (rain, snow, or extreme heat) in which the weather does not allow a user to go outside. The user can hike the same virtual path that they normally would take. Portable monitors also allow a user to record their favorite workout by walking the trail with the monitor on. Upon electrically coupling the monitor to the exercise system, the monitored activity can be downloaded to the virtual trail system attached to the exercise apparatus. The virtual trail system converts the monitored information into a workout for the exercise device. This provides the user with some exciting new benefits. For example, if it rains or snows, a user can follow their favorite hike or mountain bike trail on an exercise bike, even if there is too much rain or snow on the ground.

There are multiple methods of coding the hiking trail or hiking profile. The most prevalent and preferred embodiment is a translation of a topographical map into a workout and onto a hard coded copy of a mountain. The hard coded copy may be stored on an ASIC chip, a programmable ROM, a magnetic disk, PCMCIA card, or Compaq flash card. More specifically, the software is stored in a memory module that may be upgraded with new mountain trails or workouts. This memory module may be constructed from at least one of programmable ROM, Dynamic Memory, EEPROM, flash bios, PCMCIA cards, CD-ROM, RAM, magnetic storage disks, and Compaq flash cards. The exercise system may also provide the memory module through an electrical connection to a general-purpose computer. It may also be downloaded from an Internet site such as www.iFit.com across a communication line connection, for example via the PSTN, DSL, G-Lite, cable modem, wireless or other high-speed data connection. Particularly as the cost of wireless technology drops, a wireless connection to exercise profile sites such as iFit.com is also foreseeable.

Hiking profile coding also provides the additional advantage of recording a hike that a user might not be able to accomplish in one exercise session, especially if it is an all-day or multiple day hike. Since the average workout session lasts between about 15 minutes and 1 hour, a user would not complete longer hikes without positional cursor storage. However, the virtual trail system optionally saves the location of the user, so that upon their return to the exercise system, they are able to begin their workout where they last left off. Thus, a daylong hike of eight hours might take an individual one or two weeks to complete at thirty-minute intervals. However, the individual would have covered the same exact terrain as was covered in the original walk. In this sense, the exercise system is able to provide a user with long-term physical goals and related incentives inspiring follow-up workout sessions. This natural variety and follow-up incentive are important keys to keeping the user on a regular exercise plan.

One of the features in this invention is the interface between the display device, the controller, the adjustable exercise device, and possibly additional software. In a preferred embodiment the software is upgradeable and Internet capable. The display device is conveniently located on the exercise device or is optionally separate therefrom, such as a wall mounted or hand-held display, and provides indicator signals. Thus, the display device may be physically located on the exercise device, but may be separate therefrom in another embodiment. The controller creates codes for the display device and adjustment codes for the exercise device. The exercise device is preferably adjustable. The exercise device may act as a flat treadmill, hiker, or stepper, for example. What distinguishes this exercise system from other systems is that the user has direct control of the speed and grade. In some embodiments the system may control speed and grade during workout routines. The present invention differs from other devices, which feature time-based workouts, whereas this device uses distance-based workouts.

The display device is an example of an indicator means for displaying workout information to the user and should be positioned so that a user may easily interface with the controller and observe their progress in several categories of performance. An adjustable attachment is preferred so that users of varying sizes will have equivalent visual access. In considering construction factors such as reliability, cost, and performance, a liquid crystal display (LCD) provides the greatest flexibility for the display device. Other acceptable indicator means include LED displays, video monitors, color LCD, and flat LCD video screens. Each of these visual indicator means can be varied using colors, brightness, or synchronized pulses to represent various status conditions. Typically, the indicator means is a visual indicator, but auditory and tactile indicators may also be used as indicator means. Audio indicators may generate a full spectrum of audible noises, including music, chirping, beeping, continuous tone, or a specific audible message. Tactile indicators include vibration, texture alteration, electric tingle, generation of specific Braille characters, or the creation of a temperature variation.

FIG. 2 provides an example of a preferred embodiment of implementing the invention. This should not be seen as a limitation, however, on the arrangement or construction of the exercise apparatus. For example, in one embodiment, an LCD is employed to display clips from the actual hike or workout trail, instead of a topographical display screen.

The controller may be a microcontroller, a central processing unit (CPU), a state machine, a programmable logic array, or network of logical gates, ASIC processor, software-based controller, a combination of these components, or a variety of other controllers. Each of these controller examples are examples of processor means for electronically computing operational information based at least in part on control inputs received from the interface means. The controller receives feedback signals from the exercise apparatus and the workout profile and converts the feedback signals into control signals for the display device and exercise apparatus. Data for the controller may be stored in registers or memory modules. The controller makes adjustments to the exercise device simulating mountainous terrain. In one embodiment, the controller includes a temporary storage media for use with the display means. The temporary storage media provides a buffer for each of the displayed values, such as user age, maximum pulse and heart rate, average pulse and heart rate, target heart rate, calories burned and target calories to burn during workout session, length of workout session, and other displayed values. This multi-buffer system allows for the simple control and rapid refresh of the user workout data.

With reference now to FIG. 1, a selectively inclining and declining climbing exercise apparatus 10 of the present invention is shown. Exercise apparatus 10 supports a user ambulating thereon. Selectively inclining and declining apparatus 10 comprises a support base 12, a treadbase 14, and a handrail assembly 16. A variety of other examples of selectively inclining and declining hiking exercise apparatuses such as apparatus 10 to be employed in the present invention are disclosed in U.S. patent application Ser. No. 09/496,569 to Cutler, et al entitled "Hiking Exercise Apparatus," filed on Feb. 2, 2000, now U.S. Pat. No. 6,761,667, which is incorporated herein in its entirety by reference.

In a neutral position, treadbase 14 is parallel to a support surface. Treadbase 14 is capable of inclining to extreme angles, such that a distal end is high above the neutral position. This enables an exerciser to simulate a hiking motion that requires the user to continually lift the user's knees in an upward, outstretched manner. Treadbase 14 also declines such that a distal end thereof drops below the neutral position. Typical hikes in the mountains, for example, involve inclines and declines as well as flat surfaces. Thus, apparatus 10 is able to more closely simulate a typical mountainous terrain. A hiker traversing a hiking trail typically exhibits substantial lateral movement. Thus, treadbase 14 preferably has an aspect ratio featuring a wide treadbase 14. Examples of such aspect ratios are disclosed in the U.S. patent application to Cutler, et al entitled "Hiking Exercise Apparatus," filed on Feb. 2, 2000, which is incorporated herein in its entirety by reference as indicated above.

The coupling of treadbase 14 and the positioning of handrail assembly 16 may occur in a variety of different positions depending upon the embodiment. In the embodiment of FIG. 1, treadbase 14 is pivotally coupled at the proximal end thereof to the proximal end of support base 12. Support base 12 rests on a support surface. In the embodiment of FIG. 1, treadbase 14 comprises a treadbase frame, first and second rollers (only one roller shown) on opposite ends of the treadbase frame, and an endless belt movably mounted on the rollers.

In one embodiment, treadbase 14 is selectively moved into a position having a grade of about −30% (declined) with respect to the neutral position to about 90 degrees (inclined) with respect to the neutral position, preferably having a grade of about −120% (declined) with respect to the neutral position to about 60 degrees (inclined) with respect to the neutral position, more preferably, having a grade of about −10% with respect to the neutral position to about 100% (45 degrees) with respect to the neutral position, more preferably, having a grade of about −10% with respect to the neutral position to about 60% with respect to the neutral position. In another embodiment, treadbase 14 is selectively moved into a position having a grade of about −5% with respect to the neutral position to about 50% or 60% with respect to the neutral position.

However, these ranges are generally more of a physical limitation than an electronic limitation as the console 200 for the exercise apparatus can be configured in one embodiment to provide negative 360 degrees to positive 360-degree rotation.

By moving between these extreme ranges, an exerciser is able to simulate a hike through a variety of different slopes and angles. The virtual trail system includes an electronic console 200. Console 200 is electrically coupled to the inclination motor 18. The virtual trail system controls the amount of inclination/declination during each segment. Through the use of console 200, the user can control the amount of inclination/declination of treadbase 14, the speed of the endless belt and a variety of other features related to apparatus 10.

In one embodiment, the exercise system includes braking means for electronically slowing the speed of the operable member, such as an electronic braking system. When the exercise device exceeds a variable incline level, established by the weight of the user and the inherent resistance of the system, the force exerted on the motor of the exercise apparatus exceeds the force generated by the motor to drive the operable member of the apparatus and the electronic braking system should be activated. For hiking devices, this variable incline level can occur at approximately 15%, depending on the inherent system resistance and the forces exerted by the user. At this grade, the energy generated by the user ambulating on the exercise device exceeds the power required to drive the motor on the operable member. At inclines above about 15% the power generated by the virtual trail system exceeds approximately 100 Watts, requiring the braking means to dissipate the excess power generated by the virtual trail system. In one embodiment, the braking means of the present invention dissipates excess power generated by the virtual trail system when the power generated by the system exceeds approximately 100 Watts to approximately 700 Watts. Certain users ambulating at extreme incline settings generate excess power in the range of 500 to 700 Watts for example, depending on user and treadmill specifications.

Therefore in the preferred embodiment, the presence of excess power activates the electronic braking system, which dissipates the excess power and maintains the appropriate speed of the operable member. One method of reducing this excess power is through a feedback loop connected to the power supply for the motor, in essence reducing the power available to the motor and slowing the belt. Another method senses the presence of excess power and activates the electronic braking system by closing a switch between the motor and a power resistor, such as a heating coil resistor. This method effectively allows the motor to generate more power, but absorbs excess power via the power resistor in the required range of about 100 to about 700 watts, e.g. about 500 to about 700 watts. In one embodiment, a heating coil is provided to provide inexpensive power dissipation. However, care must be taken to disperse the heat generated by high energy levels.

In the preferred embodiment, a device cutoff system within the electronic braking system activates a forced ventilation system when heat levels begin to exceed pre-established operating ranges and in extreme cases completely cutoff the treadmill system until the detected heat levels returned to safe operating ranges. Generally, the power resistor circuit employed in the exercise device is system specific, and designed to dissipate excess power generated by the motor during to prolonged use at extreme inclines. Once the power is dissipated, the virtual trail system will open the circuit between the motor and the power resistor. In this manner the virtual trail system is able to maintain a constant speed for the operable member at high speed and high inclination settings.

Other examples of braking systems are disclosed in the U.S. patent application "Hiking Exerciser Apparatus," incorporated herein by reference.

As mentioned above, the aspect ratio, i.e., the length and width of treadbase 14 is such that climbing apparatus 10 simulates a climbing motion and allows the user the lateral movement associated therewith, yet has a minimal footprint and can be conveniently used and stored in a home or exercise gym.

Handrail assembly 16 will now be discussed in additional detail with reference to FIG. 1. The handrail assembly 16 of the present invention can be comprised of a variety of different members and have a variety of different configurations, such as those featured presently in the art. Handrail assembly 16 of FIG. 1 is coupled to the treadbase 14 such that the position of handrail assembly 16 adjusts automatically throughout the range of motion of treadbase 14. Thus, handrail assembly 16 is useful to the exerciser throughout the range of motion. Handrail assembly 16 has an operative, useful position regardless of whether treadbase 14 is in an inclined, declined, or neutral position. However, a fixed handrail assembly may also be employed which does not provide such adjustment. Handrail assembly 16 may also contain components of the feedback circuitry for monitoring the users heart rate through the physical connection created by the user's hold on the handrail assembly 16.

In the embodiment of FIG. 1, inclination motor 18, which controls the amount of inclination/declination during each segment, is part of handrail assembly 16. Handrail assembly 16 is pivotally coupled to treadbase 14 and to support base 12. Motor 18 selectively inclines and declines assembly 16, thereby selectively inclining and declining treadbase 14. However, in other embodiments, such as described in U.S. patent application to Cutler, et al entitled "Hiking Exercise Apparatus," filed on Feb. 2, 2000, which is incorporated herein in its entirety by reference as indicated above, an extension motor or other means for selectively moving the treadbase is directly coupled between the treadbase and the support base or coupled thereto in a variety of other fashions.

With reference to FIG. 2, a user console 200 contains a display device 202 and a control interface 218. Display device 202 is an example of an indicator means. Control interface 218 is an example of an interface means for receiving workout related control inputs. Display device 202 contains various workout diagnostic panels. In another embodiment of a user console, the display device of the console is located remotely from the exercise apparatus. For example, the display device may comprise a wall mounted or hand held display.

Trail workout panel 204 displays trail workout information on one panel of said user interface console 200, the trail workout information comprising at least one of: percentage of trail workout completion, relative trail elevation, distance traveled, vertical distance traveled, workout segment difficulty, remaining segment length, selected trail workout routine, and topographical information concerning the trail workout profile. In one embodiment, each of these features are present. This single glance panel provides an optimal amount of workout information to the user without distracting the user from the workout. Grade program control panel 206 includes an incline display representing the inclination of the treadmill or exercise device in degrees or grade percentage. In the embodiment of FIG. 2, the incline, terrain, or hill varies from −5% to 60% grades or −5 to 32 degrees of angular movement on the grade program control panel 206. The grade program control panel 206 may contain a terrain or hill display array that is constructed from a selectively illuminated LED display array.

The virtual trail system causes the exercise device to incline the treadbase grade or increase resistance so as to correspond to the hills displayed on the grade program control terrain display. In this manner, the user is provided with a short-term display of upcoming and/or current terrain. The grade program control panel 206 also contains a manual control indicator to signify that the user is establishing grade settings. Grade program control panel 206 further comprises a data field shown in FIG. 2 to have 21 columns with 10 indicators in each column. Although primarily configured to indicate short-term grade settings, this array of indicators may also be used to indicate any number of different parameters. For example, the grade changes can be attached to indicate speed changes. The preferred display panel configuration takes grade changes or resistance changes that are pending during the workout program and shows the changes graphically. In FIG. 2, the second to bottom horizontal row of the grade program control panel 206 would be regarded as zero, with the number of vertical blocks being illuminated to show the relative incline, grade, speed, or other value depicted. This array can be expanded to include more accuracy concerning the grade or angled inclination. As the capabilities of the exercise equipment processor increase, the display scale can be shifted.

A hike exertion panel 208 provides a single row of colored indicator LEDs summarizing the workout stress level placed upon the user. The hike exertion panel 208 divides the colored indicator LEDs into four subcategories: warm-up/cool-down, moderate hike, challenging hike, and Extreme hike. The subcategories are either based upon preprogrammed values for grade level independent of the user's response to the system and speed level or the indicator panel 208 can be a compilation and summarization of indicator panels 204, 206, 210, 212, 214, and 216 adapted to each user. In this second configuration, the hike exertion panel 208 becomes a single look pacing indicator panel considering age, heart rate, speed, grade, pace, and hike ranking. As such the hike exertion panel 208 is at least indirectly connected to the feedback circuitry, which measures the performance of the exercise equipment and/or the user.

The heart rate training zone indicator panel 210 selectively indicates age, heart rate and percentage of maximum heart rate of the user that is exercising. Training zone indicators show a user whether the current workout is proceeding above, below, or at the target heart rate for the user's age. The pulse sensor is activated after the user enters their age before the workout begins using the incremental adjustment keypad 240. In the preferred embodiment, the virtual trail system will remember a user's vitals after they renew a previous workout. Heart rate training zone indicator 210 is an extremely useful feature as it allows the trail workout to be personalized for each user, assuring that a maximum cardiovascular workout is obtained. Optional safety features in the virtual trail system include a monitor of a user's heart rate that reduces the stress or exertion levels imposed upon the user when the heart rate exceeds the target value. The stress level may be increased for a user whose heart rate is at or below the target level. These heart rate signals are received at least indirectly from the user feedback circuitry, part of the feedback means, which may collect information from a heart monitor worn, by the user or a heart monitor placed in handrail assembly 16.

Time and distance indicator panel 212 indicate the distance traveled or the segment time required for the user to travel between exercise workout segments, or the overall time required for the trail workout. Indicator panel 214 selectively provides the vertical feet traveled, the calories burned, the percentage of grade, and the maximum percentage. The time and distance indicator panel 212 and the indicator panel 214 are at least indirectly attached to feedback circuitry connected to the exercise device. Speed indicator panel 216 provides the speed presently traveled on the exercise device, or the maximum speed attained during the exercise period. The speed indicator panel 216 is indirectly attached to the feedback circuitry on the exercise device and more specifically to circuitry connected to the electronic braking system used to regulate the belt speed on the treadbase.

Control interface 218 comprises several individual adjustment keypads for interfacing with the selectively adjustable exercise apparatus. Direct grade adjustment keypad 220 allows the user to select a desired grade of an operable member of the selectively adjustable exercise apparatus through quick touch keys with pre-set percentage grade values and automatically adjust the device to the selected level. Specifically, direct grade adjustment keypad 220 has pre-set percentage grade keys for −5%, 0%, 10%, 20%, 30%, 40%, 50%, and 60%, for example, although a variety of different grades are available. The grade program controller may increase the grade or residence depending on the exercise device attached to the grade program controller. For example, a treadmill can increase the inclination of the treadbase to the desired grade. A bicycle exercise device can increase the resistance such that a comparable grade is represented. A skiing device can elevate the slope of the surface being skied upon. Similar grade or resistance adjustments can be made for other exercise devices. Inclination and declination interface buttons are also included in the direct grade adjustment keypad 220. These keys allow a user to increase or decrease the grade in 1% grade intervals, for example.

Start interface button 224 allows a user to begin the trail workout once the trail has been selected or the previous segment has been restored. Stop/Pause interface button 226 allows a user to stop or pause the workout and save the location of the user's last position on the trail for future use or allows the user to recover from overexertion. In one embodiment, Stop/Pause interface button 226 is electronically connected to an electronic braking system that prevents a user from driving the treadbase faster than the speed driven by a motor, but also for slowing the treadbase down to a stopped position so that the user won't fall of the treadbase.

As mentioned above, beginning at around a 15% grade, a hiker exercising on a treadmill may start producing more energy than is necessary to drive the treadmill belt. Thus the braking system of the present invention is useful at inclines such as in excess of about 15% grade and is particularly useful at high inclines, such as in excess of about 25% grade. The electronic braking system is electronically connected to the feedback means for calculating the actual belt speed of a given treadbase. The feedback means sends this information to the processor means for further adjustment of the treadbase to optimize to overall performance of the climbing exercise device.

Power indicators 228 show whether the proper activation key has been provided to the selectively adjustable exercise apparatus. In one embodiment, the activation key is a physical electronic key that stores the users workout information. Other embodiments may require an electronic key or password be typed in so that the workout information can be restored from a user database. Another embodiment uses a physical key as a safety measure to prevent unauthorized use of the trail exercise apparatus.

Direct speed adjustment keypad 222 allows the user to adjust the speed of the particular exercise device. Specifically, direct speed adjustment keypad 222 has keys for 0.5, 1.0, 1.5, 2.0, 3.0, 4.0, 5.0 and 6.0 mph. In addition to the aforementioned preset speed values, increase and decrease buttons increase or decrease the selectively adjustable exercise apparatus operable member speed in $\frac{1}{10}^{th}$ intervals. In the preferred treadmill configuration, the treadbase will gradually increase the belt speed according to the inputs from the user interface console 200.

Incremental adjustment keypad 240 contains an increment and decrement input keys as well as a final enter input key. One embodiment allows a user to input their age through this keypad so that the virtual trail system can customize a workout and monitoring system. Another embodiment allows a user to use this keypad to enter one or more of the following workout variables: the exerciser's age, length of workout segment, distance of workout segment, vertical feet of workout segment, maximum speed of workout segment, maximum pulse, target heart rate, maximum grade, calories to be burned, and maximum heart rate. These keys may also be used along with the trail workout panel to specifically select a workout segment for making adjustments in the present workout profile or even to select different trails. For example, the virtual trail system of FIG. 2 displays the Grand Teton trails and it is foreseeable that various popular mountain recreation areas like Mt. McKinley, Mt. Rainer, Mt. Hood, the Swiss Alps, the Ozark or Allegheny Mountains, or Mt. Everest hiking layouts can be imposed in the trail workout panel 204 using the incremental adjustment keypad 240.

The total input key 242 changes the display panels 210, 212, 214 and 216 to display their total or maximum changes. Thus an individual is enabled to see the total distance traveled, the total time of the workout, the total vertical feet traveled, the total calories burned, the average grade, and the maximum percentage. The average speed can also be indicated through the total button. In one embodiment, the results displayed when total input key 242 is pressed, are computed using registers which increment the values for the time and distance, vertical feet, and calories burned during the workout profile at variable rates depending on the amount of exercise and the speed of exercise being performed by the user. These figures are dictated by the device parameters. For example, the distance traveled in the preferred treadmill embodiment is based upon the speed of the belt on the tread base, and the distance covered by a user running upon such a base. The total calories burned would be based on the angle or the grade of the tread base and the speed of the tread base. Another embodiment includes the monitored heart rate of the individual working on the treadmill as a variable to compute the calories burned.

The select trail keypad 238 allows a user to choose a moderate, challenging, or extreme trail for their workout. In the preferred embodiment provided in FIG. 2, these trails are represented by the Teepee Glacier trail 234 as a moderate trail with workout segments A through G. The challenging trail is the Avalanche Canyon trail 230 with workout segments H through P. And the extreme trail is the Grand Teton trail 232 with workout segments R through Z. Upon choosing an exertion level, the workout will proceed along the workout segments until the trail end is obtained. These end points for the trails are represented by 236a, 236b, and 236c. In an alternative embodiment, a user can select their trail exertion level using a touch sensitive trail workout panel 204. In such an embodiment an individual can simply select a segment letter by pushing that letter or the general vicinity of that letter, and the exercise apparatus would adjust the settings to correspond to that portion or segment of the workout. It is also envisioned that various embodiments would contain trails that contained moderate, challenging, and extreme trail segments within one workout.

The iFit.com button 244 is both a selector and an indicator. The indicator light on the iFit.com button 244 demonstrates that a connection has been established between the virtual trail system and the external iFit.com system. The virtual trail system, if properly connected to either a computer or directly to the Internet through a communication line connection will use software to contact the new www.iFit.com website to obtain the services of a personal trainer. Examples of suitable communication line connections include via PSTN, DSL, G-Lite, cable modem, wireless, WAN line, radio frequency transmission, or other data connection. Once the user initiates the iFit.com session via the interface by depressing the iFit.com button 244, the virtual trail system interacts with the website to obtain digital signals for the workout session. If the online iFit.com trainer creates a "hill climb" workout for the user, the incline of the treadbase 14 will get steeper and steeper responsive to the personal trainer. The iFit.com module uses a "plug in and logon" design to make it very user friendly, even for users that are newcomers to the Internet. One advantage of the iFit.com technology is its simplicity; all the user needs to do is plug the iFit.com compatible fitness equipment into their computer, an Internet access point or PSTN access line. Once the connection is established, the workout options are endless. For example, the user can select a daily iFit workout, press "start," and the virtual trail system will begin following the daily workout profile received from the offsite database.

An alternative embodiment allows the user to participate in a live online workout session. The user designates their fitness equipment and selects a personal trainer. The trainer can adjust the equipment settings to constantly challenge the user while monitoring the user's vitals, despite the fact that the user is working out in the privacy and convenience of the user's own home. It is well known by those skilled in the art that a personal trainer helps keep a user motivated, makes the user more accountable to their goals, and helps the user achieve better results. The problem is, millions of consumers do not belong to health clubs and therefore do not have access to qualified personal trainers. Use of the iFit.com button 244 provides a new standard of fitness at home. User's can schedule a private workout session with a personal trainer conducted and monitored via computer cameras and simultaneously sent by the trainer digital signals that control the treadmill's electronic functions. As such, the present invention becomes a truly interactive personal training experience.

The iFit.com connection uses Internet "streaming" technology. Allowing consumers to quickly select and immediately begin using a workout segment without downloading the entire workout profile. The iFit.com streamable workouts are convenient and easily accessed. Furthermore, the quality of personalized workout sessions are improved, because ACE certified personal trainers develop the workouts that are sent across the iFit.com communication lines. Three predominant features are given to the present invention through the iFit.com button 244. The first is access to the basic iFit.com workout database that allows the user to change his or her workout routine every day, thereby encouraging site and workout "stickiness." The workout database streams into the user's home computer or exercise device and gives the user access to an electronic library of hundreds of preprogrammed workouts whereas most treadmills have a maximum of only 6-8 basic workouts. For example, users can adjust their treadmills to accommodate a specialized preprogrammed 20-minute fat burning workout or an 18-minute strength-training workout.

The second area of expansion are audio workouts, which give the consumer a motivating combination of heart rate paced music and the encouraging voice of a personal trainer. Digital signals in the soundtrack control: resistance, speed, and incline of the fitness equipment. The user will be able to choose from a variety of musical styles and enjoy them within the confines of their home workout area.

Finally, video workouts will stream to the virtual trail system in two categories. The first workouts are group classes and the second are hiking adventure series trails. Both types of workouts feature heart rate paced music and digital signals to control the exercise equipment. In the group class video, users will watch a fun group "sweating it up" with a motivating personal trainer leading the workout. The adventure series of workouts will combine music, digital signals, and add engaging scenes of natural beauty. One series features three hikes in the Grand Tetons. Another running adventure series will be a workout following the race course of the St. George Marathon in St. George, Utah, named by Runner's World as the most scenic marathon in America. In this manner, the hiker treadmill can be programmed to include training workouts such as the incline and distances of activities like the St. George Marathon. This would allow hiker treadmill users to practice for a marathon in another state without requiring them to travel to the location to run the course and, in essence, prepare themselves for the eventual competition without being there. While the functionality of the iFit.com button 244 is presently limited to controlling the treadmill, in the foreseeable future such workouts will interact with home stereos, TVs, VCRs, DVDs, and CDs along with the treadmill to improve the quality of the interactive feel of the exercise equipment.

One embodiment of the hiker treadmill allows the virtual trail system to interface with a program that emulates a particular climb. The program will provide virtual trail system with adjustment codes that allow the hiker device to simulate the terrain of a given hike. One method of programming a hike is through analysis of the GPS coordinates for a starting point, one or more weigh points, and an ending point. The virtual trail system will then automatically compute the distances, inclines, to simulate a hike along that course.

Figure 3:
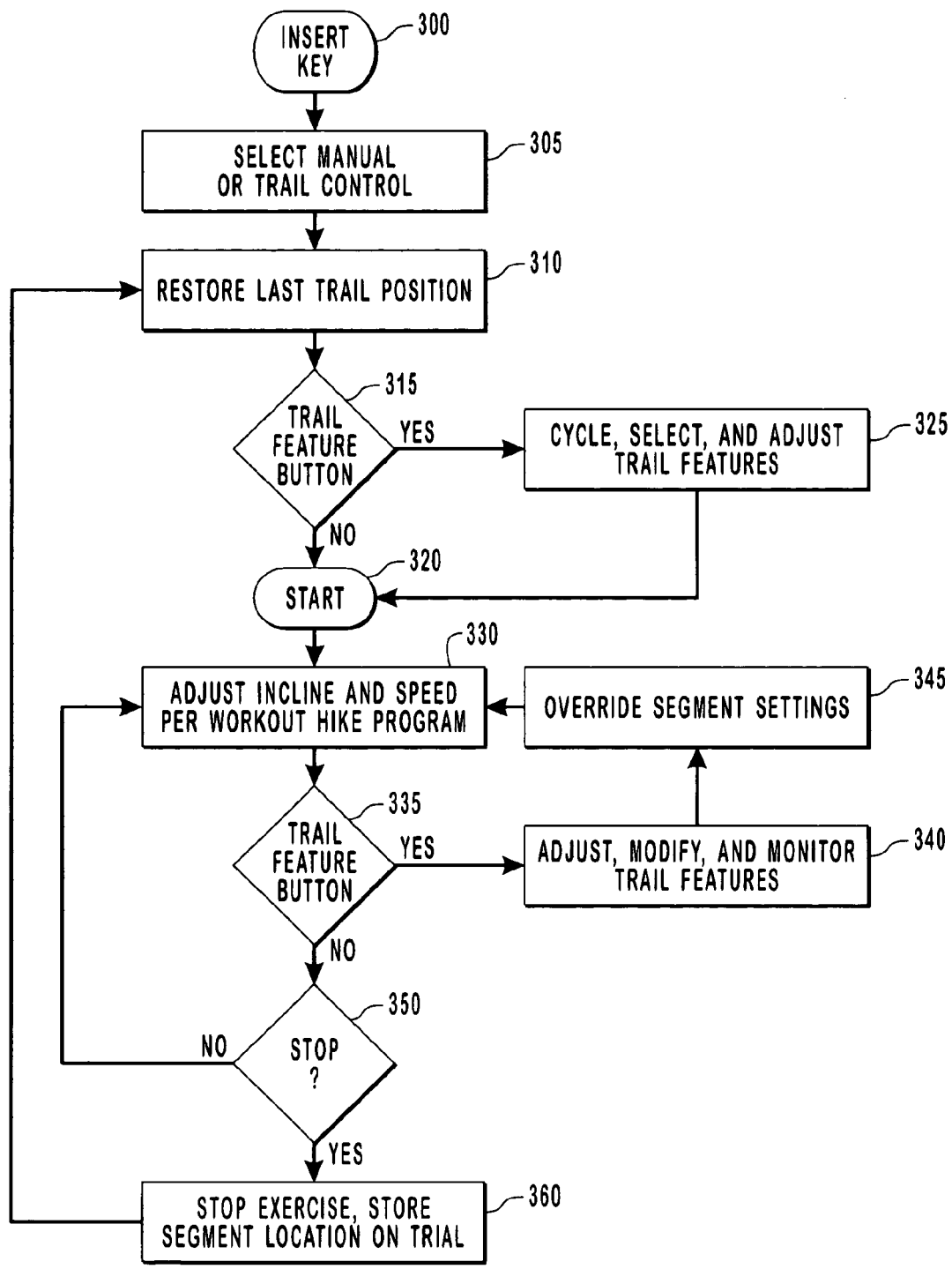
FIG. 3 is a control diagram of an interface console for a virtual trail system with trail workout incentives for an exercise system.

FIG. 3 is a control diagram for a virtual trail system with trail workout incentives incorporated into the motivational display console on an exercise device. At conditional action block 300 a user may activate the machine through the insertion or input of an access key. Selection block 305 determines whether the user desires manual or trail based workout control. If the user desires manual control, workout parameters may be established by direct adjustment keypads for grade and speed, while variable keypads may provide calorie, heart rate or other workout related restrictions. If trail based control is selected, execution block 310 will identify the user and restore the last trail position for that user. This information may be encoded into the access key or may be stored in memory relevant to the individual user. If there is no previous workout information, the user will be placed at the beginning of a trail. Decision block 315 determines whether the trail feature button has been selected. If the trail feature button has been selected, the available workout trails will cycle through and allow the user to select and adjust various trail features for the user's workout. These adjustments occur in execution block 325. If the trail feature button has not been selected, the workout will begin from the last trail position recorded according to the settings at that point. At start point 320, a conditional execution block, a user may activate the machine by pressing start. Once the exercise device starts, execution block 330 allows adjustments to inclination and speed to be made according to the workout trail program until a trail feature button is selected. If a trail feature button, as demonstrated by decision block 335 is selected, then the user is allowed to adjust, modify and monitor various trail features in execution block 340. These features include but are not limited to trail elevation change, trail distance, segment distance, segment vertical change, overall target difficulty for trail and segment, and incline or speed adjustments. Once these trail features have been adjusted, execution block 345 overrides the standard segment settings with the modified values provided in execution block 340. Generally this override occurs upon the depression of the enter button 240 or the start key 224. The controller then returns to the adjust incline and speed execution block 330 and continues with the workout segment. Upon completion of the workout segment, a stop exercise and store segment location command is executed in execution block 360. If the trail features are not manually adjusted in decision block 335, decision block 350 checks to see if the end of the workout segment has been reached. If this end point has not been obtained, the workout program returns the controller to the adjust inclination and speed execution block 330.

Figure 4:
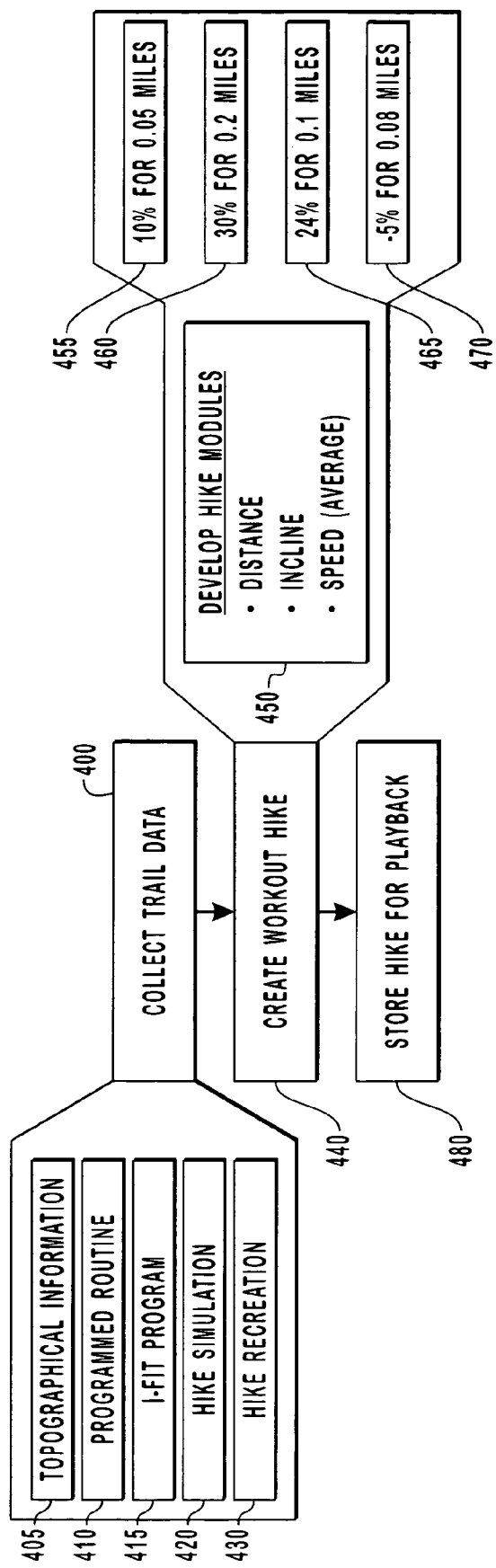
FIG. 4 is a block diagram illustrating encoding of a mountain trail, creating a workout profile, and operating a previously encoded hike.

FIG. 4 is a block diagram illustrating the process of encoding a mountain trail, the creation of a workout profile, and the standard operation of a previously encoded hike. Execution block 400 instructs an automated controller or a trail designer to collect trail data concerning the workout profile selected by the user. This data structure is comprised of various elements including a topographical information data string represented by block 405 a programmed routine represented by 410, an iFit.com program represented by block 415, a hike simulation represented by 420 and a hike recreation represented by 430. The topographical information data structure 405 might include GPS coordinates for a start point as well as one or more waypoints, segment breaks, and an end point. Associated with each one of these GPS coordinates for the waypoints, segment breakpoints, start points, and end points would be a corresponding elevation value. The controller or trail designer is then able to take this topographical information and compute the distances, the average inclinations between the waypoints, and simulate a hike from this data. Thus while a hike may include variable length workout segments as well as variable inclination adjustments.

A programmed routine 410 is comprised of inclination adjustments and distances for workout segments compiled by a trail designer to optimize the selected trail exertion. For example, a moderate trail can contain grade adjustments from negative 5% to positive 20%, while a challenging trail might include adjustments from negative 10% to positive 40% and an extreme trail can include adjustments from negative 15% to positive 60% in which some of the segments might contain drastic 20% to 30% grade changes over previous segments. The iFit.com programs 415 relate to programs available over Internet sites and allow a user to access a new trail each day.

Hike simulations 420 correspond to topographically entered information or to hike simulation inserts that may be added to the virtual trail system via PCMCIA, magnetic disk, PROM, flash upgrades, or other storage means. For example, the Grand Teton hikes displayed in FIG. 2 provide a user with a hike simulation for the Avalanche Canyon trail, the Grand Teton trail and the Teepee Glacier trail. Hike recreation 430 is data provided from a hike monitor worn by an individual during a normal workout. This is an exciting feature for the hiker as it allows an individual to perform exercise when the weather prohibits outside exercise. In essence the monitor records the distance and elevation changes during the workout period and provides that information to the exercise device through an interface or communication link.

Once the appropriate trail data is collected, execution block 440 creates a workout hike profile. The hike development module 450 collects information concerning distance, incline adjustments, and average speed traveled. The hike development module then creates individual workout segments to be chained together for an overall workout profile. Blocks 455, 460, 465 and 470 illustrate examples of workout segments. Workout segment block 465 illustrates how the grade change can occur in 1% increments. Workout block 455 demonstrates the grade 10% along with the distance 0.05 miles. This also indicates the distance factor being 0.01 miles. Workout segment block 470 demonstrates the use of a negative grade change as well as reemphasizing the potential for 0.01 miles distance changes. It is foreseeable that these grade changes can be adjusted to angular slopes and that the distances can be adopted as meters or kilometers. Once the workout profile has been assembled containing the individual workout segments, the hike is stored in execution block 480 for future playback on the exercise device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An exercise system comprising:
a support structure configured to support an operable member movably coupled to the support structure; and
a virtual trail system simulating a trail to be traversed by a user as the user exercises using the exercise system, the virtual trail system comprising:
(i) an interface console configured to adjust incline levels of said operable member and including multiple successive incline level keys and numeric indicia representative of specific incline levels corresponding to each incline level key, said interface console comprising indicator means for displaying workout information to the user at a rate proportional to the rate at which exercise is performed by the user, the indicator means displaying a topographical representation of a trail to be traversed by a user, and
(ii) a braking means for electronically slowing the speed of the operable member, wherein the braking means comprises a means for dissipating power generated by the exercise system, wherein said means for dissipating power is activated at operational points that are partially dependent on user attributes including user mass and force exerted by the user and partially dependent on virtual trail system parameters including inclination or declination positions, operating speed, and overall virtual trail system resistance.

2. The exercise system of claim 1, wherein the operable member comprises a movable treadmill belt, the incline of which changes upon selecting one of said multiple successive incline level keys.

3. The exercise system of claim 1, wherein said interface console receives workout related control inputs from the user of the exercise system and changes an incline of said operable member as a controller within said interface console computes operational information based at least in part on said control inputs.

4. An exercise system as recited in claim 1, wherein
said interface console is configured to adjust speed levels of said operable member, said interface console comprising:
a first speed level key corresponding to a first speed level of said operable member;
a second speed level key corresponding to a second speed level of said operable member that is higher than said first speed level; and
a third speed level key corresponding to a third speed level of said operable member that is higher than said second speed level,
wherein a user can directly increase said speed level of said operable member from said first speed level to said third speed level by selecting said third speed level key.

5. The exercise system of claim 4, wherein the operable member comprises a movable treadmill belt, the speed of which changes upon selecting one of said first speed level key, said second speed level key, and said third speed level key.

6. The exercise system of claim 4, wherein said interface console receives workout related control inputs from a user of the exercise system and changes a speed of said operable member as a controller within said interface console computes operational information based at least in part on said control inputs.

7. An exercise apparatus comprising:
a support base;
an operable member movably coupled to said support base; and
a virtual trail system simulating a trail to be traversed by a user as the user exercises using the exercise apparatus, the virtual trail system comprising an interface console electrically coupled to said operable member, said interface console comprising:
  (i) indicator means for displaying workout information to the user at a rate proportional to the rate at which exercise is performed by the user, the indicator means displaying a topographical representation of a trail to be traversed by a user, wherein the workout information displayed by the indicator means comprises: percentage of trail workout completion and simulated trail elevation on the same display panel; and
  (ii) a plurality of direct speed level keys selectable by a user of the exercise system, wherein each speed level key defines a pre-set speed for the exercise apparatus and is configured to initiate a change in the speed of the exercise apparatus from a current speed to said pre-set speed upon being selected by the user of the exercise apparatus wherein upon selecting one of said plurality of speed level keys, the operable member automatically adjusts from a current speed to said pre-set speed.

8. An apparatus as recited in claim 7, further comprising a plurality of direct grade level keys selectable by a user of the exercise system, wherein
each grade level key defines a pre-set grade for the exercise apparatus and is configured to initiate a change in the grade of the exercise apparatus from a current grade to said pre-set grade upon being selected by the user of the exercise apparatus, wherein upon selecting one of said plurality of grade level keys, the operable member automatically adjusts from a current grade to said pre-set grade.

9. An apparatus as recited in claim 7, wherein the virtual trail system further comprises a braking means for electronically slowing the speed of the operable member, wherein the braking means comprises a means for dissipating power generated by the virtual trail system, wherein said means for dissipating power is activated at operational points that are partially dependent on user attributes including user mass and force exerted by user and partially dependent on virtual trail system parameters including inclination or declination positions, operating speed, and overall virtual trail system resistance.

10. An apparatus as recited in claim 9, wherein the braking means dissipates excess power generated by the virtual trail system when the power generated by the system exceeds approximately 100 Watts to approximately 700 Watts.

11. An apparatus as recited in claim 7, wherein the system displays a pre-designed trail having at least a beginning point and an end point, said pre-designed trail selectively including at least one midway point.

12. An apparatus as recited in claim 11, wherein said system comprises means for selecting a pre-designed trail containing routines including the average grade and distance to be traveled between the beginning point, the end point, and the selective midway points.

13. An apparatus as recited in claim 7, wherein the workout information displayed by the display comprises percentage of trail workout completion and elevation on the same panel.

14. An apparatus as recited in claim 7, wherein the indicator means comprises a plurality of workout segments represented between two points on a trail and wherein the segments reflect an average slope change between said two points.

15. An apparatus as recited in claim 7, wherein the system comprises a processor selected from the group consisting of a controller, state machine, microprocessor, embedded system, and other means for processing and displaying information.

16. An apparatus as recited in claim 7, wherein the interface console comprises:
a first speed level key corresponding to a first speed level of said operable member;
a second speed level key corresponding to a second speed level of said operable member that is higher than said first speed level; and
a third speed level key corresponding to a third speed level of said operable member that is higher than said second speed level,
wherein a user can directly increase said speed level of said operable member from said first speed level to said third speed level by selecting said third speed level key.

17. An apparatus as recited in claim 7, wherein the interface console further comprises:
a first incline level key corresponding to a first incline level of said operable member;
a second incline level key corresponding to a second incline level of said operable member that is greater than said first incline level; and
a third incline level key corresponding to a third incline level of said operable member that is greater than said second incline level,
wherein a user can directly increase said incline level of said operable member from said first incline level to said third incline level by selecting said third incline level key.

18. An apparatus as recited in claim 7, wherein the interface console further comprises an incremental control configured to incrementally change one of said plurality of pre-set speed levels selected by the user of the exercise system.

19. An apparatus as recited in claim 7, wherein the interface console further comprises:
a direct grade adjustment keypad, said direct grade adjustment keypad comprising a plurality of preset grade keys, each key of said plurality of grade keys corresponding to a single preset operating grade of said operable member, wherein one touch of any of the preset grade keys changes any current operating grade of said operable member to the operating grade corresponding to the touched key.

20. An exercise system comprising:
a support base;
an operable member movably coupled to said support base; and
a virtual trail system simulating a trail to be traversed by a user as the user exercises using the exercise system, the virtual trail system comprising:
a control interface coupled to the operable member, the control interface enabling a user to control the operable member, the control interface comprising:
  (i) indicator means for displaying workout information to the user at a rate proportional to the rate at which exercise is performed by the user, the indicator means displaying a topographical representation of a trail to be traversed by a user, wherein the virtual trail system displays a pre-designed trail having at least a beginning point and an end point, said pre-designed trail selectively including at least one midway point, and wherein the virtual trail system comprises means for selecting a pre-designed trail containing routines including the average grade and distance to be traveled between the beginning point, the end point, and the selective midway points; and (ii) a direct adjustment keypad having a plurality of speed level keys, each of the plurality of speed level keys being associated with one of a plurality of pre-set speeds such that upon contacting any one key, the speed level of the operable member changes to the speed of the contacted key regardless of the current speed level of the exercise apparatus.

21. An exercise system comprising:
a support base;
an operable member movably coupled to said support base; and
a virtual trail system simulating a trail to be traversed by a user as the user exercises using the exercise system, the virtual trail system comprising:
an interface console electrically coupled to said operable member, said interface console comprising:
  indicator means for displaying workout information to the user at a rate proportional to the rate at which exercise is performed by the user, the indicator means displaying a topographical representation of a trail to be traversed by a user, wherein the workout information displayed by the display comprises percentage of trail workout completed and elevation on the same panel; the interface console further comprising:
  a first incline level key corresponding to a first incline level of said operable member;
  a second incline level key corresponding to a second incline level of said operable member that is greater than said first incline level; and
  a third incline level key corresponding to a third incline level of said operable member that is greater than said second incline level, wherein a user can directly increase said incline level of said operable member from said first incline level to said third incline level by selecting said third incline level key; and wherein said interface console is configured to adjust speed levels of said operable member, said interface console further comprising:
  a first speed level key corresponding to a first speed level of said operable member;
  a second speed level key corresponding to a second speed level of said operable member that is higher than said first speed level; and
  a third speed level key corresponding to a third speed level of said operable member that is higher than said second speed level, wherein a user can directly increase said speed level of said operable member from said first speed level to said third speed level by selecting said third speed level key.

22. An exercise system as recited in claim 21, further comprising means for selecting a pre-designed trail containing routines including the average grade and distance to be traveled between a beginning point, an end point, and at least one midway point of the pre-designed trail.

23. An exercise system as recited in claim 21, wherein the workout information displayed by the indicator means comprises: percentage of trail workout completion and simulated trail elevation on the same display panel.

24. An exercise system, comprising:
a support base;
an operable member movably coupled to said support base; and
a virtual trail system simulating a trail to be traversed by a user as the user exercises using the exercise system, the virtual trail system comprising an interface console electrically coupled to said operable member, and wherein said interface console comprises: indicator means for displaying workout information to the user at a rate proportional to the rate at which exercise is performed by the user, the indicator means displaying a topographical representation of a trail to be traversed by a user, wherein the indicator means comprises a plurality of workout segments represented between two points on a trail and wherein the segments reflect an average slope change between said two points; wherein said interface console is configured to adjust speed levels of said operable member, said interface console further comprising:
  a first speed level key corresponding to a first speed level of said operable member;
  a second speed level key corresponding to a second speed level of said operable member that is higher than said first speed level; and
  a third speed level key corresponding to a third speed level of said operable member that is higher than said second speed level, wherein a user can directly increase said speed level of said operable member from said first speed level to said third speed level by selecting said third speed level key.

25. An exercise system as recited in claim 24, further comprising an incremental grade control configured to incrementally adjust a grade of the operable member.

26. An exercise system as recited in claim 24, wherein the workout information displayed by the indicator means comprises: percentage of trail workout completion and simulated trail elevation on the same display panel.

27. An exercise apparatus comprising:
a support base;
an operable member movably coupled to said support base; and
a virtual trail system simulating a trail to be traversed by a user as the user exercises using the exercise apparatus, the virtual trail system comprising:
an interface console configured to adjust speed levels of said operable member, said interface console comprising:
  indicator means for displaying workout information to the user at a rate proportional to the rate at which exercise is performed by the user, the indicator means displaying a topographical representation of a trail to be traversed by a user, wherein the workout information displayed by the indicator means comprises: percentage of trail workout completion and simulated trail elevation on the same display panel; said interface console further comprising:
  a first speed level key corresponding to a first speed level of said operable member;
  a second speed level key corresponding to a second speed level of said operable member that is higher than said first speed level; and
  a third speed level key corresponding to a third speed level of said operable member that is higher than said second speed level, wherein a user can directly increase said speed level of said operable member from said first speed level to said third speed level by selecting said third speed level key.

28. The exercise apparatus of claim 27, wherein said interface console receives workout related control inputs from a user of the exercise system and changes an incline of said operable member as a controller within said interface console computes operational information based at least in part on said control inputs.

29. The exercise apparatus of claim 27, wherein the operable member comprises a treadmill treadbase, the grade of which changes upon selecting a direct grade adjustment key associated with the interface console.

30. The exercise apparatus of claim 27, wherein the operable member comprises a movable treadmill belt, the speed of which changes upon selecting a speed level key.

31. The exercise apparatus of claim 27, wherein said interface console receives workout related control inputs from a user of the exercise system and changes a speed of said operable member as a controller within said interface console computes operational information based at least in part on said control inputs.

32. An exercise apparatus comprising:
a support base;
an operable member movably coupled to said support base; and
a virtual trail system simulating a trail to be traversed by a user as the user exercises using the exercise apparatus, the virtual trail system comprising an interface console electrically coupled to said operable member, said interface console comprising indicator means for displaying workout information to the user at a rate proportional to the rate at which exercise is performed by the user, the indicator means displaying a topographical representation of a trail to be traversed by a user, wherein the virtual trail system displays a pre-designed trail having at least a beginning point and an end point, said pre-designed trail selectively including at least one midway point, and wherein the virtual trail system comprises means for selecting a pre-designed trail containing routines including the average grade and distance to be traveled between the beginning point, the end point, and the selective midway points; wherein said interface console is configured to adjust speed levels of said operable member, said interface console further comprising:
a first speed level key corresponding to a first speed level of said operable member;
a second speed level key corresponding to a second speed level of said operable member that is higher than said first speed level; and
a third speed level key corresponding to a third speed level of said operable member that is higher than said second speed level, wherein a user can directly increase said speed level of said operable member from said first speed level to said third speed level by selecting said third speed level key.

33. An exercise apparatus of claim 32, wherein the operable member comprises a treadmill treadbase, a grade of which changes upon selecting a direct grade adjustment key associated with a console of the exercise system.

34. A treadmill, comprising:
a support base;
a treadbase coupled to said support base; and
a virtual trail system simulating a trail to be traversed by a user as the user exercises using the exercise treadmill, the virtual trail system comprising indicator means for displaying workout information to the user at a rate proportional to the rate at which exercise is performed by the user, the indicator means displaying a topographical representation of a trail to be traversed by a user, wherein the workout information displayed by the indicator means comprises: percentage of trail workout completion and simulated trail elevation on the same display panel; and
an interface console electrically coupled to said treadbase, said interface console having a direct adjustment keypad, said direct adjustment keypad comprising a plurality of preset keys, each key of said plurality of keys corresponding to a single preset operating parameter of said treadbase, wherein one touch of any of said preset keys changes any current operating parameter of said treadbase to the operating parameter corresponding to the touched key regardless of the level of the current operating parameter, wherein the direct adjustment keypad comprises:
a first grade level key corresponding to a first grade level of said treadbase;
a second grade level key corresponding to a second grade level of said treadbase that is higher than said first grade level; and
a third grade level key corresponding to a third grade level of said treadbase that is higher than said second grade level, wherein a user can directly increase said grade level of said treadbase from said first grade level to said third grade level by activating said third grade level key.

35. A treadmill as recited in claim 34, wherein the treadbase comprises a moveable treadmill belt, the speed of which changes upon selecting a direct speed adjustment key.

36. An exercise apparatus as recited in claim 34, wherein said interface console is configured to adjust speed levels of said operable member, said interface console comprising:
a first speed level key corresponding to a first speed level of said operable member;
a second speed level key corresponding to a second speed level of said operable member that is higher than said first speed level; and
a third speed level key corresponding to a third speed level of said operable member that is higher than said second speed level,
wherein a user can directly increase said speed level of said operable member from said first speed level to said third speed level by activating said third speed level key.

37. An exercise apparatus comprising:
a support base;
an operable member movably coupled to said support base; and
a virtual trail system simulating a trail to be traversed by a user as the user exercises using the exercise apparatus, the virtual trail system comprising:
an interface console electrically coupled to said operable member, said interface console comprising:
(i) indicator means for displaying workout information to the user at a rate proportional to the rate at which exercise is performed by the user, the indicator means displaying a topographical representation of a trail to be traversed by a user wherein the workout information displayed by the indicator means comprises percentage of trail workout completion and simulated trail elevation on the same display panel; and
(ii) a plurality of direct grade level keys selectable by a user of the exercise system, wherein each grade level key defines a pre-set grade for the exercise apparatus and is configured to initiate a change in the grade of the exercise apparatus from a current grade to said pre-set grade upon being selected by the user of the exercise apparatus, wherein upon selecting one of said plurality of grade level keys, the operable member automatically adjusts from a current grade to said pre-set grade.

38. A system as recited in claim 37, further comprising a direct adjustment keypad having a plurality of speed level keys, each of the plurality of speed level keys being associated with one of a plurality of pre-set speeds such that upon contacting any one key, the speed level changes to the speed of the contacted key regardless of the current speed level of the exercise apparatus.

39. A system as recited in claim 37, wherein upon touching one of the plurality of grade level keys, the operable member is adjusted to a pre-set grade associated with the touched key.

40. A system as recited in claim 37, further comprising an incremental grade control.

41. The exercise system in claim 37 wherein the operable member comprises a treadmill treadbase, and wherein selection of a preset key changes a grade of the treadmill treadbase to a grade corresponding to the selected key regardless of the current grade of the treadmill treadbase.

42. The system as recited in claim 37, wherein said interface console comprises a plurality of direct speed adjustment keys, each of said plurality of direct speed adjustment keys being associated with a single preset speed of said operable member, each of said plurality of direct speed adjustment keys being selectable to automatically change any current speed of said operable member to the single preset speed associated with the selected direct speed adjustment key of said plurality of direct speed adjustment keys.

43. An apparatus as recited in claim 37, wherein the interface console further comprises a direct adjustment keypad configured to adjust the speed of the operable member, said direct adjustment keypad comprising a plurality of keys, each key of said plurality of keys corresponding to only one pre-set speed, wherein a touch of any one key of said plurality of keys changes any current speed of the operable member to the pre-set speed corresponding to the touched key.

* * * * *

UNITED STATES PATENT AND TRADEMARK OFFICE
CERTIFICATE OF CORRECTION

| | |
|---|---|
| PATENT NO. | : 7,645,212 B2 |
| APPLICATION NO. | : 11/113921 |
| DATED | : January 12, 2010 |
| INVENTOR(S) | : Ashby et al. |

It is certified that error appears in the above-identified patent and that said Letters Patent is hereby corrected as shown below:

On Title Page 3, Item 56 Right Column
Change reference "Horizon Fitness Elite 2.0T, Elite 3.0T, Elite 4.0T, Elite 5.0T Treadmill Owner's Guide, pp. 1-40, available on information and belief at lease as early as 2004." to --Horizon Fitness Elite 2.0T, Elite 3.0T, Elite 4.0T, Elite 5.0T Treadmill Owner's Guide, pp. 1-40, available on information and belief at least as early as 2004.--

Title Page 4, Item 56 Left Column
Change reference "Trackmaster Online: History http://web/archive.org/web/19991012112927/www.trackmastertreadmills.com/history.html, available on information and belief at least as early as Oct. 1999, 1 page." to --Trackmaster Online: History http://web.archive.org/web/19991012112927/www.trackmastertreadmills.com/history.html, available on information and belief at least as early as Oct. 1999, 1 page.--

Title Page 5, Item 56 Left Column
Change reference "Transcript of Deposition of Michael Benjamin, taken Apr. 11, 2007, from Cybergym Reaserch, LLC v. Icon Health & Fitness, et al., in the Eastern District f Texas, Marshal Dividion, Case No. 2:05-cv-527 DF, 33 pages." to --Transcript of Deposition of Michael Benjamin, taken Apr. 11, 2007, from Cybergym Research, LLC v. Icon Health & Fitness, et al., in the Eastern District of Texas, Marshal Division, Case No. 2:05-cv-527 DF, 33 pages.--
Change reference "Cybergear, Inc., CyberGear 1000 brochure, which was available, on information and belief, as least as early as 1994, 2 pages." to --Cybergear, Inc., CyberGear 1000 brochure, which was available, on information and belief, at least as early as 1994, 2 pages.--

Signed and Sealed this
Eleventh Day of September, 2012

David J. Kappos
*Director of the United States Patent and Trademark Office*

Title Page 5, Item 56 Right Column
Change reference ""Virtual Treadmill Takes Users Anywhere They Want to Go," http://www.ksl/com/?nid=148&sid=6920538, Jun. 24, 2009, 2 pages." to --"Virtual Treadmill Takes Users Anywhere They Want to Go," http://www.ksl.com/?nid=148&sid=6920538, Jun. 24, 2009, 2 pages.--

Change reference ""Icon Health & Fitness Inc.'s Supplemental Preliminary Invalidity Contentions," Case No. 2-05-cv-527, signed by Brent A. Hansen on Jun. 23, 2006." to --Icon Health & Fitness Inc.'s Supplemental Preliminary Invalidity Contentions," Case No. 2:05-cv-527, signed by Brent A. Hansen on Jun. 23, 2006.--

Change reference ""Icon Health & Fitness Inc.'s Preliminary Invalidity Contentions," Case No: 2-05-cv-527, signed by Brent A. Hansen on Jun. 26, 2006." to --"Icon Health & Fitness Inc.'s Preliminary Invalidity Contentions," Case No. 2:05-cv-527, signed by Brent A. Hansen on Jun. 26, 2006.--

Drawings, Sheet 3
Replace FIG. 3 with the figure depicted herein below, wherein "TRIAL" has been changed to --TRAIL-- in box 360

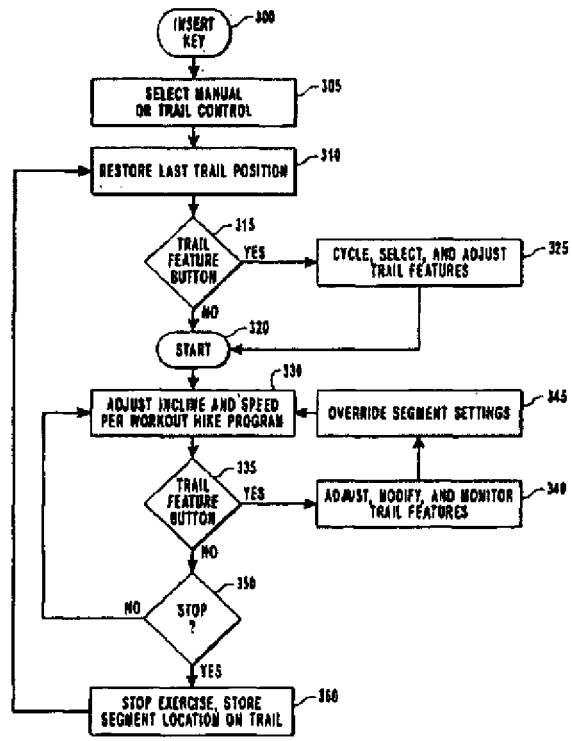

FIG. 3

Column 3
Line 6, delete "be"

Column 4
Line 7, change "on part" to --in part--
Line 23, change "on" to --on a--
Line 65, change "on to" to --onto--

Column 8
Line 41, change "returned" to --return--
Line 45, delete "to"

Column 10
Line 11, change "Extreme" to --extreme--
Line 44, change "indicate" to --indicates--

Column 11
Line 3, change "residence" to --resistance--
Line 24, change "of" to --off--
Line 35, change "to overall" to --the overall--
Line 40, change "users" to --user's--

Column 12
Line 5, change "Rainer" to --Rainier--

Column 13
Lines 28-29, change "technology. Allowing" to --technology, allowing--

Column 14
Line 16, change "virtual" to --the virtual--
Line 20, change "weigh points" to --waypoints--

Column 15
Line 11, change "405" to --405,--